United States Patent
Shultz et al.

(10) Patent No.: US 6,703,211 B1
(45) Date of Patent: Mar. 9, 2004

(54) CELLULAR DETECTION BY PROVIDING HIGH ENERGY PHOSPHATE DONOR OTHER THAN ADP TO PRODUCE ATP

(75) Inventors: John William Shultz, Verona, WI (US); Keith V. Wood, Madison, WI (US); Mary Hall, Madison, WI (US); Tamara Sue Pratt, Monticello, WI (US)

(73) Assignee: Promega Corporation, Madison, WI (US)

( * ) Notice: Subject to any disclaimer, the term of this patent is extended or adjusted under 35 U.S.C. 154(b) by 0 days.

(21) Appl. No.: 09/396,334

(22) Filed: Sep. 15, 1999

Related U.S. Application Data

(63) Continuation-in-part of application No. 09/252,436, filed on Feb. 18, 1999, now Pat. No. 6,159,693, which is a continuation-in-part of application No. 09/042,287, filed on Mar. 13, 1998, now Pat. No. 6,335,162.

(51) Int. Cl.[7] .............. C12Q 1/02; C12Q 1/04; C12Q 1/66
(52) U.S. Cl. ................. 435/8; 435/29; 435/34
(58) Field of Search ............... 435/4, 8, 243, 435/29, 34

(56) References Cited

U.S. PATENT DOCUMENTS

| | | | |
|---|---|---|---|
| 3,929,583 A | 12/1975 | Sharpe et al. | |
| 4,303,752 A | 12/1981 | Kolehmainen et al. | |
| 4,331,762 A | 5/1982 | Nakajima et al. | |
| 4,338,395 A | 7/1982 | Leon et al. | |
| 4,352,881 A | 10/1982 | Inagawa et al. | |
| 4,357,420 A | 11/1982 | Bostick et al. | |
| 4,368,261 A | 1/1983 | Klose et al. | |
| 4,371,611 A | 2/1983 | Fusee | |
| 4,383,031 A * | 5/1983 | Boguslaski et al. ............ | 435/7 |
| 4,394,445 A | 7/1983 | Nix et al. | |
| 4,415,655 A | 11/1983 | De Castro et al. | |
| 4,438,124 A | 3/1984 | Meister et al. | |
| 4,443,594 A | 4/1984 | Buckmann | |
| 4,446,231 A | 5/1984 | Self | |
| 4,460,684 A | 7/1984 | Bauer | |
| 4,485,177 A | 11/1984 | Siedel et al. | |
| 4,587,213 A | 5/1986 | Malecki | |
| 4,595,655 A | 6/1986 | Self | |
| 4,629,688 A * | 12/1986 | Bolguslaski et al. ........... | 435/7 |
| 4,683,195 A | 7/1987 | Mullis et al. | |
| 4,683,202 A | 7/1987 | Mullis et al. | |
| 4,735,897 A | 4/1988 | Vary et al. | |
| 4,743,561 A | 5/1988 | Shaffar | |
| 4,755,458 A | 7/1988 | Rabbani et al. | |
| 4,791,055 A * | 12/1988 | Boguslaski et al. ........... | 435/7 |
| 4,800,159 A | 1/1989 | Mullis et al. | |
| 4,908,236 A | 3/1990 | Pitt et al. | |
| 5,229,285 A | 7/1993 | Kajiyama et al. | |
| 5,356,776 A | 10/1994 | Kambara et al. | |
| 5,366,867 A | 11/1994 | Kawakami et al. | |
| 5,389,512 A | 2/1995 | Snisky | |
| 5,391,480 A | 2/1995 | Davis et al. | |
| 5,399,491 A | 3/1995 | Kacian et al. | |
| 5,403,711 A | 4/1995 | Walder et al. | |
| 5,416,002 A | 5/1995 | Steele et al. | |
| 5,445,933 A | 8/1995 | Eadie et al. | |
| 5,494,810 A | 2/1996 | Barany et al. | |
| 5,498,523 A | 3/1996 | Tabor et al. | |
| 5,512,439 A | 4/1996 | Hornes et al. | |
| 5,516,663 A | 5/1996 | Backman et al. | |
| 5,530,192 A | 6/1996 | Murase et al. | |
| 5,541,311 A | 7/1996 | Dahlberg et al. | |
| 5,561,044 A | 10/1996 | Walker et al. | |
| 5,573,906 A | 11/1996 | Bannwarth et al. | |
| 5,622,824 A | 4/1997 | Koster et al. | |
| 5,627,042 A * | 5/1997 | Hirose et al. .................. | 435/8 |
| 5,648,232 A | 7/1997 | Squirrell | |
| 5,656,207 A * | 8/1997 | Woodhead et al. ......... | 252/700 |
| 5,660,988 A | 8/1997 | Duck et al. | |
| 5,667,964 A | 9/1997 | Ho | |
| 5,683,868 A * | 11/1997 | LaRossa et al. ............... | 435/6 |
| 5,683,877 A | 11/1997 | Lu-Chang et al. | |
| 5,691,146 A | 11/1997 | Mayrand | |
| 5,719,113 A | 2/1998 | Fendler et al. | |
| 5,723,591 A | 3/1998 | Livak et al. | |
| 5,731,146 A | 3/1998 | Duck et al. | |

(List continued on next page.)

FOREIGN PATENT DOCUMENTS

| | | |
|---|---|---|
| EP | 0 229 601 A | 11/1986 |
| EP | 639 647 A | 7/1994 |
| EP | 0 663 447 A | 12/1994 |
| EP | 0 894 867 A | 11/1997 |
| GB | 2055200 | 12/1981 |

(List continued on next page.)

OTHER PUBLICATIONS

A.E. Sippel, "Purification and Characterization of Adenosine Triphosphate: Ribonucleic Acid Adenyltransferase from *Escherichia coli*" *Eur. J. Biochem.* 37:31–40 (1973).

K.Chowdhury, N. Kaushik, V.N. Pandey and M.J. Modak, "Elucidiation of the Role of Arg 110 of Murine Leukemia Virus Reverse Transcriptase in the Catalytic Mechanism: Biochemical Characterization of Its Mutant Enzymes," *Biochemistry*, 35:16610–16620 (1996).

S. Karamohamed, M. Ronaghi and P. Nyren, "Bioluminometric Method for Real–Time Detection of Reverse Transcriptase Activity", *Biotechniques*, 24:302–306 (Feb., 1998).

(List continued on next page.)

*Primary Examiner*—David M. Naff
*Assistant Examiner*—Deborah K. Ware
(74) *Attorney, Agent, or Firm*—Welsh & Katz, Ltd.

(57) ABSTRACT

Processes and materials are disclosed for the detection of cells using endogenous enzymes to catalyze the conversion of AMP and/or ADP to ATP in the presence of a high energy phosphate donor other than ADP, then the ATP is detected using luciferase.

20 Claims, No Drawings

U.S. PATENT DOCUMENTS

| | | | |
|---|---|---|---|
| 5,736,365 A | | 4/1998 | Walker et al. |
| 5,741,635 A | | 4/1998 | Boss et al. |
| 5,756,011 A | * | 5/1998 | Woodhead et al. ......... 252/700 |
| 5,759,820 A | | 6/1998 | Hornes et al. |
| 5,763,181 A | | 6/1998 | Han et al. |
| 5,766,849 A | | 6/1998 | McDonough et al. |
| 5,786,139 A | | 7/1998 | Burke et al. |
| 5,786,183 A | | 7/1998 | Ryder et al. |
| 5,811,251 A | * | 9/1998 | Hirose et al. .................. 435/8 |
| 5,814,031 A | | 9/1998 | Mooney et al. |
| 5,814,491 A | | 9/1998 | Vijg et al. |
| 5,824,517 A | | 10/1998 | Cleuziat et al. |
| 5,834,202 A | | 11/1998 | Auerbach |
| 5,840,873 A | | 11/1998 | Nelson et al. |
| 5,843,660 A | | 12/1998 | Schumm et al. |
| 5,849,547 A | | 12/1998 | Cleuziat et al. |
| 5,853,981 A | | 12/1998 | Kondo et al. |
| 5,854,033 A | | 12/1998 | Lizardi |
| 5,861,242 A | | 1/1999 | Chee et al. |
| 5,863,736 A | | 1/1999 | Haaland |
| 5,866,337 A | | 2/1999 | Schon |
| 5,869,252 A | | 2/1999 | Bouma et al. |
| 5,871,902 A | | 2/1999 | Weininger et al. |
| 5,876,924 A | | 3/1999 | Zhang et al. |
| 5,876,930 A | | 3/1999 | Livak et al. |
| 5,876,978 A | | 3/1999 | Willey et al. |
| 5,876,995 A | * | 3/1999 | Bryan ........................ 435/189 |
| 5,880,473 A | | 3/1999 | Ginestet |
| 5,882,856 A | | 3/1999 | Shuber |
| 5,885,775 A | | 3/1999 | Haff et al. |
| 5,888,819 A | | 3/1999 | Goelet et al. |
| 5,902,722 A | | 5/1999 | Di Cesare et al. |
| 5,981,178 A | | 11/1999 | Tsui et al. |
| 6,007,987 A | | 12/1999 | Cantor et al. |
| 6,017,722 A | * | 1/2000 | Becvar et al. .................. 435/8 |
| 6,066,483 A | | 5/2000 | Riggs et al. |
| 6,261,537 B1 | * | 7/2001 | Klaveness et al. ......... 424/9.52 |
| 2002/0025940 A1 | * | 2/2002 | Whitney ...................... 514/44 |

FOREIGN PATENT DOCUMENTS

| | | |
|---|---|---|
| WO | WO 90/05530 | 5/1990 |
| WO | WO 91/17264 | 11/1991 |
| WO | WO 92/13963 | 8/1992 |
| WO | WO 94/25619 | 11/1994 |
| WO | WO 95/21938 | 8/1995 |
| WO | WO 96/41014 | 12/1996 |
| WO | WO 97/41256 | 11/1997 |
| WO | WO 98/13523 | 4/1998 |
| WO | WO 98/54362 | 4/1998 |
| WO | WO 98/28440 | 7/1998 |

OTHER PUBLICATIONS

B. Hove–Jensen, K.W. Harlow, C.J. King, R.L. Switzer, "Phosphoribosylpyrophosphate Synthetase of *Escherichia coli*", *J. Biol. Chem.*, 261(15):6765–6771 (1986).

P. Nyren, S. Karamohamed and M. Ronaghi, "Detection of Single–Base Changes Using a Bioluminometric Primer Extension Assay", *Anal. Biochem.*, 244:367–373 (Jan. 15, 1997).

M. Ronaghi, S. Karamohamed, B. Pettersson, M. Uhlen and P. Nyren, "Real–Time DNA Sequencing Using Detection of Pyrophosphate Release," *Anal. Biochem.*, 242:84–89 (1996).

T.A. Rozovskaya, V.O. Rechinsky, R.S. Bibilashvili, M.Y. Karpeisky, N.B. Tarusova, R.M. Khomutov, H.B.F. Dixon, "The Mechanism of Pyrophosphorolysis of RNA by RNA Polymerase", *Biochem. J.*, 224: 645–650 (1989).

M.P. Deutscher and A. Kornberg, "Enzymatic Synthesis of Deoxyribonucleic Acid", *J. Biol. Chem.*, 244(11):3019–28 (1969).

J.D. Moyer and J.F. Henderson, "Nucleoside Triphosphate Specificity of Firefly Luciferase", *Anal. Biochem.*, 131:187–189 (1983).

C. Blondin, L. Serina, L. Weismuller, A. Gilles and O. Barzu, "Improved Spectrophotometric Assay of Nucleoside Monophosphate Kinase Activity Using the Pyruvate Kinase/Lactate Dehydrogenase Coupling System", *Anal. Biochem.*, 220:219–21 (1994).

S. Tabor and C.C. Richardson, "DNA Sequence Analysis With a Modified Bacteriophage T7 DNA Polymerase", *J. Biol. Chem.*, 265(14):8322–8328 (1990).

R.S. Chittock, J.–M. Hawronsky, J. Holah and C.W. Wharton, "Kinetic Aspects of ATP Amplification Reactions", *Anal. Biochem.*, 255:120–126 (Jan. 1, 1998).

Kung, et al., "Picogram Quantitation ofTotal DNA Using DNA–Binding Proteins in a Silicon Sensor–Based System", *Anal. Biochem.*, 187:220–227 (1990).

Srivastavan & Modak, *J. Biol. Chem.*, 255(5):2000–2004 (1980).

Sano & Feix, *Eur. J. Biochem.*, 71:577–583 (1976).

Sabina, et al., *Science*, 223:1193–1195 (1984).

Parks & Agarwal in *The Enzymes*, vol. 9:307–333, P. Boyer Ed. (1973).

Shimofuruy & Suzuki, *Biochem. Intl.*, 26(5):853–861 (1992).

Nyren, et al., "Detection of Single–Base Changes Using a Bioluminometric Primer Extension Assay", *Anal. Biochem.*, 244:367–373 (1997).

P. Bernard et al., *Am. J. Pathol.*, 153:1055–1061 (1998).

G. Garinis et al., *J. Clin. Lab. Anal.*, 13:122–125 (1999).

Holguin, et al., *Eur. J. Clin. Microbiol. Infect. Dis.*, 18:256–259 (1999).

Boriskin, et al., *Arch. Dis. Child.*, 80:132–136 (1999).

De Vega, et al., "Primer Terminus Stabilizing at the 3'–5' exonuclease active site of _29 DNA polymerase. Involvement of two amino acid residues highly conserved in proofreading DNA polymerases", *EMBO J.*, 15(5):1182–1192 (1996).

S. Patel et al., *Biochemistry*, 30:511–525 (1991).

I. Wong et al., *Biochemistry*, 30:526–537 (1991).

S. Zinnen et al., *J. Biological Chemistry*, 269(39):24195–24202 (1994).

J. Lindquist, Dept. of Bacteriology, University of Wisconsin–Madison, http://www.bact.wisc.edu/bact102/102dil3.html.

J. Lindquist, Dept. of Bacteriology, University of Wisconsin–Madison, http://www.bact.wisc.edu/bact102/102dil3a.html.

"Most Probable Number (MPN)", Water Quality Association Glossary of Terms (1997) (no author listed) printed Sep. 6, 1999 from www.WQA.org/WQIS/Glossary/mpn.htm.

P. Nyren, B. Pettersson, and M. Uhlen. "Solid Phase DNA Minisequencing by an Enzymatic Luminometric Inorganic Pyrophosphate Detection Assay,"*Anal. Biochem.*, 208:171–175 (1993).

M. Ronaghi, S. Karamohamed, B. Pettersson, M. Uhlen, and P. Nyren, "Real–Time DNA Sequencing Using Detection of Pyrophosphate Release," *Anal. Biochem.*, 242:84–89 (1996).

J. Shultz, D. Leippe, K. Lewis, R. Lyke, M. Nelson, C. Reynolds, "Detection of Low Levels of Nucleic Acids by Enzymatic Conversion to Substrates for Luciferase", pp. 1–9, Poster presented at a Protein Society meeting in San Diego, California Jul. 1998.

Heid, et al., "Real Time Quantitative PCR", *Genome Research*, 6:986–994 (1996).

Nagano, et al., "Detection of Verotoxin–Producing *Escherichia coli* O157:H7 by Multiplex Polymerase Chain Reaction", *Microbiol. Immunol.*, 42(5), 372–376 (1998).

Sherlock, et al., "Assessment of diagnostic quantitative fluorescent multiplex polymerase chain reaction assays performed on single cells", *Ann. Hum. Genet.* 62:9–23 (1998).

Axton, et al., "A Single–Tube Multiplex System for the Simultaneous Detection of 10Common Cystic Fibrosis Mutations", *Human Mutation*, 5:260–262 (1995).

Poyser et al., "Multiplex genotyping for cystic fibrosis from filter paper blood spots", *Ann. Clin. Biochem.*, 35:611–615 (1998).

Caudai, et al., "Detection of HCV and GBV–C/HGV injection by multiplex PCR in plasma samples of transfused subjects", *J. Virol Meth.*, 70: 79–83 (1998).

Songsivilai, et al., "Improved Amplification System for Detection of Hepatitis C virus Genome that Simultaneously Differentiates Viral Genotype", *Southeast Asian J. Trop. Med. Public Health*, 27(2): 237–243 (1996).

Oyofo, et al., "Detection of Enterotoxigenic *Escherichia coli*, Shigella and Campylobacter spp. by Multiplex PCR Assay", *J. Diarrhoeal Dis. Res.*, 14(3): 207–210 (1996).

L. Ripoll, et al., "Multiplex PCR–mediated Site–directed Mutagenesis for One–step Determination of Factor V Leiden and G20210A Transition of the Prothrombin Gene", pp. 960–961 (1997).

L. Ripoll, et al., "Multiplex ASA PCR for a Simultaneous Determination of Factor V Leiden Gene, G—A 20210 Prothrombin Gene and C—T 677 MTHFR Gene Mutations", *Thromb Haemost*, 79:1054–1055 (1998).

X. Xu et al., "Two Multiplex PCR–Based DNA Assays for the Thrombosis Risk Factors Prothrombin G20210A and Coagulation Factor V G1691A Polymorphisms", *Thrombosis Research* 93:265–269 (1999).

E. Gomez, et al., "Rapid Simultaneous Screening of Factor V Leiden and G20210A Prothrombin Variant by Multiplex Polymerase Chain Reaction on Whole Blood", *Blood* 91(6): 2208–2211 (1998).

D. Linfert, et al., "Rapid Mutiplex Analysis for the Factor V Leiden and Prothrombin G20210A Mutations Associated with Hereditary Thrombophilia", *Connecticut Medicine* 62(9):519–525 (1998).

P. Nyren, et al., *Anal. Biochem.*, 244:367–373 (1997).

S. Borman, "Developers of Novel DNA Sequencers Claim Major Performance Advances", *C&EN*, pp. 37–40 (Jul. 24, 1995).

P. Belgrader, et al., "PCR Detection of Bacteria in Seven Minutes", *Science Magazine* 284:449–450 (1999).

K. Hayashi *Genetic Analysis: Techniques and Applications* 9:73–79 (1992).

Newton et al., *Nucl. Acids Res.*, 17:2503–2516 (1989).

Wu et al., *Proc. Natl. Acad. Sci., USA*, 86:2757–2760 (1989).

T. Nikiforov, et al., *Nucl. Acids Res.*, 22:4167–4175 (1994).

C. Wittwer, et al., *Biotechniques*, 22:130–138 (1997).

P. Holland, et al., *Proc. Natl. Acad. Sci., USA*, 88:7276–7280 (1991).

R. Kramer, et al., *Nat. Biotechnol.*, 14:303–308 (1996).

J. Shultz, D. Leippe, K. Lewis and M. Nelson, "Non–radioactive Measurement of DNA Using Coupled Enzymatic Reactions", pp. 1–12, Presentation Mar. 16–20, 1998 at a Parenteral Drug Association meeting in San Francisco, California.

Seq ID No. 1, "Blast Archaeal Gemone Sequences at Center of Marine Biotechnology" Online, May 21, 1999, Retrieved on Aug. 7, 200 http://Combdna.umbi.umd.edu/bags.html. http://Comb5–156.umbi.umd.edu/cgi–bin/PfurGene-.PL?GeneID=894645&Dataset=Nayb&Geneidtxt–994645, Online! XP002144446, Retrieved from the internet on Aug. 7, 2000.

Giartosio, et al., "Thermal stability of hexameric and tetrameric nucleoside diphosphate kinases: Effect of subunit interaction", *J. Biol. Chem.*, 271(30):17845–17851 (1996).

Bi, W., et al., "Detection of known mutation by proof–reading PCR", *Nucleic Acid Research*, GB, 26(12):3073–3075 (1998).

Kawarabayashi, et al., "Complete Sequence and Gene Organization of the Genorne of hyper–thermophilic Archaebacteriurn, *Pyrococcus horikoshii* OT3", *DNA Research*, 5:55–76 (1998).

* cited by examiner

CELLULAR DETECTION BY PROVIDING HIGH ENERGY PHOSPHATE DONOR OTHER THAN ADP TO PRODUCE ATP

CROSS-REFERENCE TO RELATED APPLICATIONS

This application is a continuation-in-part of U.S. Ser. No. 09/252,436, now U.S. Pat. No. 6,159,693 filed on Feb. 18, 1999, which is a continuation-in-part of U.S. Ser. No. 09/042,287, now U.S. Pat. No. 6,335,162 filed Mar. 13, 1998, both of which are incorporated herein by reference.

FIELD OF THE INVENTION

The invention relates to cellular detection. More specifically, the invention relates to the indirect detection of cells by the detection of ATP in a reaction mixture.

BACKGROUND OF THE INVENTION

The ability to detect very low amounts of cells such as microbes is required in a variety of fields, both where sterilization is necessary and where the presence of microbes is expected as in foods and commercial water sources. By traditional methods, it is generally not possible to detect and quantify very small amounts of microbes directly from a sample. For example, a research scientist may want to know how many cells they have in a sample. A typical way of estimating this is to grow the cells in liquid culture and then to measure the optical density of the culture.

Reducing the amount of microbes to required levels is important in the making of consumer products, such as food and medical products. This is accomplished by autoclaving, irradiation, pasteurization, and filtration, among other techniques. A task of quality control is to ascertain the effectiveness of these techniques. Typically, such is the work of microbiologists, who attempt to grow cultures from swabs or samples of the product to be tested. On the other hand, commercial water sources are expected to contain low concentrations of microbes and microbiologists also grow cultures from these to determine their microbial counts in those sources.

In the food science and water treatment fields, liquid samples are typically analyzed using the Most Probable Number (MPN) method. The Most Probable Number method is basically a statistical analysis based on classical bacteriology culturing techniques, wherein in a range of dilutions of a liquid sample are inoculated into growth medium, and cell growth in the medium is detected. Standard MPN procedures often use a minimum of three dilutions and multiple culture tubes at each level of dilution. A typical worker would consult an MPN table to obtain the statistical multiplier to calculate the most probable number of bacterial cells in the original sample based on the growth distribution in the culture tubes.

Methods such as MPN are useful for calculating the number of living cells in a sample. The living cells in a consumer product are likely to grow during storage or after it is opened. The growth of these cells may adversely affect the consumer.

The time it takes to carry out an analysis by methods such as MPN that rely on the culturing of cells is a major drawback. The analyst must wait for the cultures to grow. Culture growth typically takes from overnight to several days.

All living organisms use adenosine triphosphate (ATP) as an energy source. In the prior art, cells are detected by assaying for the presence of ATP using the ATP-driven chemiluminescent (bioluminescent) luciferase/luciferin couple according to the following reaction.

luciferase

$$ATP+luciferin+O_2 \rightarrow AMP+oxyluciferin+PPi+hv.$$

The light that is emitted from the reaction (hv) is conveniently measurable.

The amount of ATP present in a sample has been used to infer the amount of microbial organisms since the mid-1960s, according to U.S. Pat. No. 5,648,232, citing other work. Chittock et al., *Analyt. Biochem.*, 255:120–126 (1998), discuss the detection of ATP on a food preparation surface as a marker for biological contamination. A firefly luciferase/luciferin system is used to detect the ATP that is present in a sample. In the art discussed in that publication, commercial systems have a detection limit of about 5 pg ATP. Chittock, et al. disclose a method to achieve that detection limit using a less sensitive luminometer and Michaelis kinetics to calculate the time at which the bioluminescence reaches one-half of its maximal value to calculate the initial ATP concentration. Chittock, et al. note that adenylate kinase activity can be driven by excess CTP, which is not a substrate of luciferase, and that adenylate kinase can convert AMP to ATP, citing Brovko et al., *Anal. Biochem.*, 220:410–414 (1994).

U.S. Pat. No. 5,648,232 discloses a more sensitive way to detect microorganisms using a luciferase ATP assay. Rather than to detect only the ATP present at the time of measuring (linear relationship between photons produced and the amount of ATP), those workers detect the presence of adenylate kinase, an enzyme that catalyzes the conversion of ADP to ATP. By providing ADP, a single adenylate kinase molecule can give rise to an amplified amount of light by converting multiple ADP molecules to ATP and AMP. Those workers report that typically 400,000 ADP molecules are converted to ATP by a single adenylate kinase molecule in 10 minutes. The method disclosed in that patent for determining the presence and/or amount of microorganisms and/or their intracellular material present in a sample involves lysing the cells, providing adenosine diphosphate (ADP), luciferase/luciferin and preferably magnesium ions, and then analyzing for light produced from the luciferase/luciferin reaction.

An advantage to the method of U.S. Pat. No. 5,648,232 over mere analysis for the ATP that is present in a sample is that ATP can be present for a number of reasons, but the presence of adenylate kinase means that a living organism is likely present.

A drawback of that method is that solutions of ADP are unstable, resulting in formation of ATP. Thus, in a method of that patent, ADP is preferably kept in solid form until immediately prior to use. Contamination of the ADP, particularly with ATP, is highly undesirable for a cellular assay based on ATP detection. That patent advises purchasing high purity commercial ADP (>99.5% purity), then further purifying the ADP by column chromatography.

International Patent Application Publication No. WO/94/25619 discusses the art of the detection of biological material. Cyclic reactions for the measurement of low levels of NAD(H) or NADP(H) were discussed therein, citing EP-A-0060123, linearly amplifying the detection target, thus requiring a long time for sensitive measurements. WO/94/25619 cites GB-A-2055200 for disclosing a linear amplification of ATP using adenylate kinase to catalyse the reaction of AMP and ATP to form 2 ADP, which is then re-phosphorylated by pyruvate kinase to form ATP. In GB-A-2055200, the ATP is measured using bioluminescence and a luminometer.

The same cycle is discussed therein citing Chittock et al., *Biochem. Soc. Trans.*, 19:160S (1991), wherein adenylate kinase forms two ADP from an AMP and an ATP. Pyruvate kinase then converts the two ADP to two ATP. Chittock et al. close the cycle by permitting luciferase to convert an ATP back to AMP, producing bioluminescence.

WO/94/25619 itself discloses a method of detecting ATP indirectly, by using ADP to convert glucose-6-phosphate to glucose with glucose kinase, then detecting the glucose product, the concentration of which increases exponentially when sufficient AMP is present with adenylate kinase to reform the consumed ADP. They add glucokinase and adenylate kinase and glucose-6-phosphate to determine ATP present.

It would be beneficial if a method were available for fast, highly sensitive detection of the presence of very low amounts of cells. The disclosure that follows provides such a method that also solves the problem posed by the instability of ADP by providing AMP and a high energy phosphate donor that are stable, as alternative precursors to ATP, and uses endogenous cellular enzymes to convert those precursors to ATP, as described below.

BRIEF SUMMARY OF THE INVENTION

The invention contemplates a method for determining the presence and/or amount of cells in an aqueous sample composition. The method contemplates indirectly detecting cellular enzymes that convert AMP into ATP. The process includes providing a high energy phosphate donor, and preferably also providing AMP, and detecting the generated ATP. Such a method comprises the following steps. An aqueous sample solution to be assayed for the presence of cells is admixed with a high energy phosphate donor (other than ADP) to form a reaction mixture. The reaction mixture is maintained for a time period sufficient for enzymes endogenous to the cells to convert the AMP to ATP. The reaction mixture is assayed for the presence of ATP. An amount of ATP greater than that in a control indicates the presence of cells in the aqueous sample. Preferably, the conditions are favorable for phosphate transfer, such as an excess of phosphate donor relative to acceptor.

Preferably, the ATP is assayed using a Coleoptera-type luciferase enzyme, such as firefly luciferase, most preferably a thermostable luciferase. Preferably, the reaction mixture further comprises the luciferase. Preferably, the reaction mixture further comprises a high energy phosphate donor other than ADP, most preferably dCTP. It is also preferred to have magnesium ions in the reaction mixture.

In a preferred embodiment of the invention, the aqueous sample solution is a test sample wherein the cells have been treated by a physical method such as sonication or a series of freeze/thaw cycles or by admixture with a chemical agent or agents that lyse or otherwise disrupt the cellular membrane. Such a treatment serves to permeabilize or disrupt the membranes of the cells. Preferably the chemical agent or agents comprise an extractant, most preferably polymixin B sulfate and/or chlorhexidine.

In contemplated embodiments, the sample source is a solid or liquid. Contemplated sample sources are consumer products or materials used in the manufacture of a consumer product; examples include foods and beverages, cosmetics, medicinals and pharmaceuticals. It is further contemplated that the sample is a commercial or residential source of water.

In a further preferred embodiment, a sample source has been filtered to retain cells, thus forming a test sample. Most preferably, the cells on the filter, the test sample, are treated to form an aqueous sample composition. Thus a contemplated aqueous sample is a solid in contact with a liquid. In an alternative embodiment of such an aqueous sample composition, a solid sample source is analyzed directly by wetting the solid (admixing) with a solution containing a high energy phosphate donor, luciferase, and luciferin and detecting the light produced. Preferably, such a solid sample source is treated, most preferably by also admixing with an extractant.

The invention further contemplates a kit for the detection of cells that comprises purified high energy phosphate donor, preferably dCTP, purified luciferin and purified luciferase. Preferably, the luciferase is a thermostable luciferase such as Luc146-1H2. A contemplated kit further comprises purified AMP, and optionally, magnesium ions. It is further contemplated that the kit comprises an extractant, preferably comprising polymixin B sulfate and/or chlorhexidine.

The present invention has many benefits and advantages, several of which are listed below.

One benefit of the invention is that its use provides results more rapidly than classical culturing methods.

An advantage of the invention is that it is very sensitive, able to detect as few as 4 cells in an aqueous sample.

Another benefit of the invention is that that the cellular detection is possible despite a large background of ATP in the sample source.

Yet another advantage of the invention is the enhanced stability of the reagents for cellular detection.

Still further benefits and advantages of the invention will become apparent from the specification and claims that follow.

Definitions

To facilitate understanding of the invention, a number of terms are defined below.

The term "isolated" when used in relation to an organic molecule such as luciferase, luciferin, AMP, or dCTP, refers to a molecule that is identified and separated from at least one contaminant with which it is ordinarily present. Thus, an isolated molecule is present in a form or setting that is different from that in which it is found in nature. In contrast, non-isolated molecules are found in the state they exist in nature.

As used herein, the term "purified" or "to purify" means the result of any process that removes some contaminants from the component of interest. The percent of a purified component is thereby increased in the sample.

The term "sample source," as used herein, is used in its broadest sense. A "sample source" is suspected of containing a cell or is an intermediate to the formation of the "aqueous sample" that is analyzed. The phrase "aqueous sample" contemplates a liquid solution, an emulsion or a suspension, and a solid in contact with a liquid. The location of the aqueous sample is not limited to a traditional reaction vessel. For example the solid sample source may be a solid or porous material supporting a liquid film. A "test sample" contemplates a sample that is derived from a sample source The term "detection," as used herein, refers to quantitatively or qualitatively determining the presence or absence of a component within a sample.

DETAILED DESCRIPTION OF THE INVENTION

The present invention contemplates a process for the indirect detection of the presence of cells in an aqueous sample by detecting light produced from ATP that is generated in the reaction from AMP and a high energy phosphate donor using endogenous cellular enzymes admixed with exogenously supplied AMP a high energy phosphate donor.

A process of the invention differs from known cellular detection methods in that it relies upon cellular endogenous enzymes to use the provided high energy phosphate donor to produce a light signal. In preferred embodiments, the more stable AMP is provided, as opposed to the relatively unstable ATP precursor, ADP, as provided in a method of U.S. Pat. No. 5,648,232.

A method of the invention is able to detect the presence of cells that are viable or only recently degraded. Because a process of the invention uses endogenous cellular enzymes, loss (or absence) of the activity of those enzymes results in the lack of a signal. Cell death, for example as a result of most sterilization processes tends to result in enzyme inactivity. Cells tend to lyse upon death, and enzymes once contained in intact cells will denature or are degraded.

The types of cells that can be detected by a process of the invention include: prokaryotes such as bacteria, eukaryotic cells, archael cells, fungi, plant and animal cells. A method of the invention is particularly useful for detecting bacterial contamination. As noted before, all living things use ATP as an energy source and therefore have enzymes capable of catalyzing the conversion of AMP and a high energy phosphate donor to ATP as required by the process of the invention.

The invention contemplates that samples containing a very large number of cells are diluted, preferably serially, to come within accurate ranges of detection when the amount of cells present is sought. A contemplated method is very sensitive, as shown in the Examples herein.

The process for detecting the presence of cells taught herein is not useful for the determination of the kinds of cells (speciation) with the exception of the distinction between eukaryotic and prokaryotic cells as discussed herein with regard to the use of certain extractants. For a determination of the types of cells present, useful processes are disclosed in the parent, copending applications U.S. Ser. No. 09/252,436, filed on Feb. 18, 1999, which is a continuation-in-part of U.S. Ser. No. 09/042,287, filed Mar. 13, 1998.

The detection of ATP using a contemplated process can be quantitative. The addition of known quantities of ATP to samples prepared according to the invention result in standard curves that are useful for the determination of ATP concentrations in the samples. The linear response range exists for several powers of ten. The addition of ATP directly to a sample results in an additive effect on the light signal produced.

Adenosine exists in a cell in any of its three interconvertible forms: AMP, ADP and ATP. The combined total of the three is the "adenosine pool" of a cell. The relative amounts of the three forms depends upon the energy state of the cell, for example dormant cells have less of the ATP form. It was known in the art to detect cells by measuring the ATP form that was exogenous in a cell. Thus, it was more difficult to detect dormant cells than active cells. The present invention solves that problem by providing a high energy phosphate donor and permitting endogenous enzyme activity to convert the entire adenosine pool to the ATP form.

Some workers in the art suggested enhancing a cellular ATP detection signal by adding exogenous ADP and permitting endogenous adenylate kinase and phosphate donors to convert the added ADP to additional ATP. The present invention contemplates the provision of AMP in addition to the high energy phosphate donor to enhance ATP-generated light output.

The cellular adenosine pool provides insight into the cellular enzyme concentration, and thus the number of cells present. As shown in the Examples hereinafter, the light signal produced is proportional to the number of cells in a sample. Thus, a process of the present invention is useful for the determination of the presence and/or amount of cells in a sample.

The present invention provides methods for determining the presence and/or amount of cells and cellular material present in the sample. In some embodiments of this invention, cells are treated to make the added phosphate donor (D-P) accessible to endogenous enzymes. In other embodiments, high energy phosphate donor molecules and AMP molecules are then added to the treated cells. It is believed that the primary pathway resulting in ATP formation proceeds through the formation of ADP molecules. ADP molecules produced by the enzymatic transfer of a phosphate group from the high energy donor to AMP according to the following reaction:

The reaction is catalyzed by endogenous enzymes present in the reaction mixture. It is further believed that a primary pathway for ATP formation includes the enzymatic transfer of a phosphate from the donor molecules to adenosine 5'-diphosphate molecules according to the following reaction:

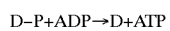

The ADP phosphorylation reaction is also catalyzed by endogenous enzymes present in the reaction mixture. Thus, the endogenous cellular components provide various enzymatic activities such as nucleotide monophosphate kinase (NMPK) activity and nucleotide diphosphate kinase (NDPK) activity, whose combined effect results in the production of ATP. In particularly preferred embodiments, the ATP is then detected by either a luciferase detection system or NADH detection system. The AMP are endogenous or can be exogenously supplied as discussed hereinabove.

A. Samples

A process of the invention utilizes an aqueous sample composition. The sample composition can be made from a variety of sample sources, including test samples. Samples can be obtained from liquids, such as inter alia beverages, drinking water, liquid waste and runoff. Test samples can also be obtained from gases for example, by adhesion of the cells or microorganisms to a solid surface and then extracting them or the cell contents into a solution, or by bubbling the gas through a liquid, for example an extractant. U.S. Pat. No. 5,773,710 provides an apparatus for such gas sampling. Test samples can also be taken from solids for example, by swabbing a surface (e.g. a manufacturing surface) and swirling the swab in a liquid for analysis, or by suspension of a solid sample (e.g. a food sample) in a liquid.

The invention contemplates that the reactions typically occur in solution although some bacterial sample sources are a solid, for example by swabbing a surface or forcing air through a filter. It is contemplated that for such a solid sample source, an aqueous sample is made by adding the filter to the extractant to permit the high energy phosphate donor access to the enzymatic activities needed to perform the necessary phosphate transfers. Alternatively, the cells may be treated directly on a solid surface providing for detection from the surface.

A process of the invention is useful for quality control and monitoring. The process is useful in the food processing and manufacturing, waste treatment, and medical fields. Gas sampling is useful in manufacturing under sterile conditions, military biological warfare monitoring, and hospitals and treatment wards. Solid sampling is useful in manufacturing and medical fields.

B. Lysis

Treatment to lyse or disrupt a cell is not essential in a process of the invention. However, it is preferred to at least permeabilize the cell, thereby leading to better access to endogenous enzymes. Such treatment also enhances the reproducibility of results from a process of the invention. Thus, for optimum detection of cells, it is preferred to disrupt or otherwise break down the cells so that intracellular enzymes for converting AMP to ATP are released or otherwise exposed to the provided reagents.

Methods for permeabilization, lysis or disruption of cells are well known in the art. A wide variety of equipment is available for mechanical disruption, including sonicators (ultrasonic generators) and French presses. Cells can be disrupted by osmotic shock, by treatments such as a series of freeze-thaw cycles, or a rapid alteration of the ionic strength of the environment, or by the use of agents that directly disrupt cell membranes such as enzymes like lysozyme or chemical agents such as detergent or surfactants and antibacterials such as polymixin B and chlorhexidine.

Such chemical reagents are commercially available and commonly referred to as "extractants". Typical extractants include general cationic detergents such as CTAB (cetyl trimethyl ammonium bromide), anionic detergents such as sodium dodecyl sulfate and nonionic surfactants such as poloxyethylene alkyl phenyl ethers (e.g. Tritons®, from Sigma, St. Louis, Mo.), nonoxynols, or other materials such as polymixin B sulfate or chlorhexidine, and proprietary formulae such as Extractant™ (F352A, Promega Corp., Madison, Wis.) and Celsis-Lumac (1290142, Celsis, Evanston, Ill.).

A typical concentration for such detergents for use in disrupting cells ranges from about 0.01% to 10.0% in an aqueous solution. Cationic detergents are known to release the contents of eukaryotic cells as well as all other kinds of cells. In contrast, the use of a non-ionic detergent is effective for releasing materials from eukaryotic cells without disturbing other kinds of cells. Thus, one can distinguish between bacterial cells versus eukaryotic cells.

The Examples hereinafter show that some extractants or combinations thereof affect more than others the light signal produced from the luciferase/luciferin couple, and thus the sensitivity. Such effects can be lessened using other chemical additives. For very sensitive cellular detection, a preferred cell treatment solution combines about 0.05 to about 2 mg/mL of polymixin B sulfate with about 0.01 to about 10 percent chlorhexidine, preferably about 0.5 to about 1.5 mg/mL polymixin B sulfate with about 0.2 to about 6 percent chlorhexidine, and most preferably about 1 mg/mL polymixin B sulfate and about 0.05 percent chlorhexidine. Preferably, the chlorhexidine is added just prior to use.

Some variation in the sensitivity of detection of the same type of cells between stationary phase cultures and log phase cultures is reported below in Example 22. It is noted that the presence of the cells is detected using a method of the invention in either situation.

C. Filtration

Filtration is desirable in some cases as a step in testing a liquid or gaseous sample by a process of the invention. A filtration step can serve two purposes i) collection of cells, and ii) isolation of cells. Filtration is preferred when a sample is taken from a large volume of a dilute gas or liquid.

Filtration serves to minimize sampling error from dilute sources. One skilled in the art understands that with dilute sources, "sampling error" is not really a measurement error, but rather it is a reality of the sample. When a liter of solution contains only 5 cells, there are many one milliliter samples of that liter that cannot contain a single cell. Thus, the larger the sample, the smaller the error. Filtering a large volume permits a concentration of the cells from within that large volume into a known small volume.

Because of the sensitive detection method used herein, such concentration is not always required to achieve a signal. As is evident from the Examples hereinafter, dilution of the resuspension from the filter is often desired before luminescence detection.

Filtering also serves to isolate the cells from their source. This isolation is often desirable for sensitive, reproducible assays. As the Examples hereinafter demonstrate, there are some components of a sample source that can inhibit light generation from the luciferase/luciferin reaction. A filtration step can also serve to separate the sought after cells from the offending component of the sample source.

Similarly, a filtration step can be used to transfer the cells to be assayed to a solution that provides a lower background. For example, a source with a large amount of ATP outside of the cells can be filtered to isolate the contaminating bacteria, and then the bacteria can be washed to further remove adhering ATP from the source. For example, fruit juices contain very high amounts of "background" ATP.

Filtration materials and methods for the removal or isolation of cells are well known to those in the art. Materials have advanced significantly since the 1970s from the standpoint of the ability to retain microorganisms effectively while passing a large volume relatively rapidly. Advanced manufacturing techniques make available highly homogenous separation materials. A large array of filters are available with a variety of size cut-offs and membrane hydrophobicities and charges. Thus, one can select for the retention of certain types of microorganisms over others.

One skilled in the art will appreciate that many of the materials and methods for the isolation of cells can be substituted for a filtration step in preparing a sample for analysis by a contemplated process. Such methods include immunological concentration of cells, centrifugation, as well as buffer exchange or washing to remove background signal contributors. Dialysis methods serve equally well for removal of background signal contributors, and to a certain extent for concentration.

For many applications of a process of the invention, standard 0.2 micron cut-off membranes (e.g. 0.22 micron Millipore® Express Membrane, Millipore Corp., Bedford, Mass. or those available from Fisher Scientific, Pittsburgh, Pa.) can be used.

As mentioned above, washing of the isolated cells, preferably with a non-disrupting low or no-background solution is an optional step to decrease background signal. Exemplary washes include buffers for the extractant omitting the extractant, or a Tris-buffered saline solution. Typically, the wash buffer is not such as to cause osmotic shock (lysis) or otherwise disturb the membrane integrity of the cells or microorganisms.

D. Luciferase/Luciferin Reaction

The luciferase/luciferin reaction is well known in the art, and there are commercial sources for the necessary reagents as well as protocols for their use. For example, several luciferase/luciferin reagents along with luciferase are available from Promega Corp., Madison, Wis. Commercially available luciferases include firefly luciferase (*Photinus pyralis*, "Ppy luciferase"). Purified beetle luciferin is also commercially available from Promega.

Other luciferases useful in a process of the invention include thermostable luciferases, such as the thermostable Luc90-1B5 luciferase, and other mutants, Luc133-1B2 luciferase and Luc146-1H2 luciferase. Thermostable luciferases are preferred in a process of the invention because they are resistant to the destabilizing effect of the materials used to permeabilize the cells, i.e. chemicals such as chlorhexidine. Further, contaminating adenylate kinase activity can often be easily reduced from a luciferase preparation by heat denaturation of the adenylate kinase (e.g. from the non-thermostable cell in which a recombinant luciferase is produced). The thermostable Luc146-1H2 luciferase is disclosed in copending U.S. Patent Application, "Thermostable Luciferases and Methods of Production", filed Sep. 15, 1999, is a continuation-in-part of U.S. application Ser. No. 09/156,946 filed in December 1998, the disclosures of both of which are incorporated herein by reference. Embodiments of the invention using thermostable luciferases are preferred.

It has been found that the stability of the luciferase enzyme is enhanced by the addition of a stabilizer, such as bovine serum albumin (BSA) or gelatin. BSA or gelatin may also have a stabilizing effect on the cellular enzymes that are responsible for the phosphate transfer. Due to the tendency of commercially available BSA to contain adenylate kinase, ATP and other impurities, it is preferable to use gelatin (0.1 to 2 percent by weight) in a contemplated process.

The luciferase/luciferin reaction is well-known in the art for the detection of ATP. The reaction conditions are also well known. Several exemplary reaction conditions are in the Examples below and in the parent applications listed above, incorporated herein by reference.

In a contemplated embodiments, ATP detection reagent referred to as L/L reagent (Promega, FF2021) is utilized. Most preferably, the luciferase/luciferin reagent comprises a thermostable luciferase in a compatible buffer containing luciferin, such as the solution that is used in Examples 20–23, below.

The amount of luciferase used in a 100 $\mu$L reaction is 1–100 $\mu$g, preferably, about 1 to 10 $\mu$g.

The pH value of the reaction should be between about pH 4.5 and pH 9. The currently available luciferase enzymes are active in that pH range. Low activity was noted at pH 4.5 in Example 20. Preferably, the pH value is about pH 7 to about pH 8, most preferably, about pH 7.2. The temperature range is preferably about zero degrees C to about 80° C. In embodiments of the invention using non-thermostable luciferases, the reaction temperature is preferably about 15° C. to about 35° C., most preferably about 22° C. In preferred embodiments using the thermostable luciferases, a pretreatment temperature to remove contaminating enzyme activity is preferably about 50° C. to about 80° C., most preferably about 65° C., and the reaction temperature for the thermostable enzymes is as with the non-thermostable luciferase enzymes. A heat pretreatment step is preferably one to ten minutes long, however if contaminating enzyme activity such as adenylate kinase activity is still higher than desired at that time, a repeat or longer time is useful.

When a sample is taken from a solution that does not interfere with the luciferase reaction, there is no need to wash the cells prior to analysis. Phenol red can interfere with the luciferase reaction. Extractant™ (Promega F3532A) inhibits the reaction slightly, but that affect is ameliorated by the presence of Triton® N-101 (nonoxynol-10). Chlorhexidine also negatively affects the light production, and that negative affect is also ameliorated by Triton® N-101. Coenzyme A was found to slightly negatively affect the reaction results.

Although it is recognized that proper controls can account for impurities in the reagents and buffers, it is preferable to use reagents with as high a purity as possible for all reagents. The presence of ATP, or particularly, enzymes such as adenylate kinase (both common in luciferase preparations) can skew the results and cause a high background signal.

Preferably, magnesium ions are provided in a process or kit according to the invention, most preferably as $MgCl_2$, $Mg(OCOCH_3)_2$, or $MgSO_4$. It is recognized by those skilled in the art that other forms of magnesium ions serve equally well, and further that other ions can serve as substitutes for magnesium ions (e.g. $Mn^{2+}$ or $Ca^{2+}$). It is also noted that magnesium ions tend to be ubiquitous to the extent that the addition of exogenous magnesium ions is not necessary to practice the invention. However, the provision of magnesium ions is preferred for maximal reproducibility and sensitivity.

As is evident from the luciferase/luciferin reaction above, oxygen is a reactant of the reaction. Therefore, the reaction should not be conducted under anaerobic conditions. However, it is not generally necessary in practicing the invention to provide oxygen over an above that present in the air. Reactions can take place in closed vessels, provided there is sufficient oxygen in the reaction solution.

As shown in the Examples hereinafter, the luciferase reactions can be conveniently conducted in a plate with multiple reaction wells. The light readings can be conducted therein with the proper equipment.

The preparation of the assay preferably involves the preparation and running of appropriate controls, preferably including a sample that does not contain permeabilizing agents. Another desirable control is a heat treated sample that is devoid of background adenylate kinase activity.

In a contemplated process of the present invention, enhanced sensitivity of a cellular detection process of the invention is a result of the addition of exogenous adenosine monophosphate (AMP) and a high energy phosphate donor. The exogenous AMP is converted by endogenous cellular enzymes, in the presence of a high energy phosphate donor, into ATP, which is detected using the luciferase/luciferin reaction, thereby showing the presence of cells or microorganisms.

In an embodiment of the invention, a high energy phosphate donor for AMP is provided that is not a preferred substrate for luciferin. Moyer and Henderson, *Anal. Biochem.*, 131:187–189 (1983), note that although ATP is the preferred substrate for firefly luciferase, other nucleotides dATP, XTP, UTP, GTP, TTP, dUTP, CTP, dGTP, ITP, dITP, dCTP can act as substrates, but are less than $\frac{1}{50}$ as active as ATP. Moyer and Henderson concluded that these other nucleotides can contribute to the background but are negligible with respect to their effect on ATP detection. Thus, any of those nucleotides can be used as high energy phosphate donors for the conversion of AMP to ATP.

The present invention provides methods utilizing different substrates for detecting the presence of cells or microorganisms in a liquid sample (preferably a lysate) suspected of containing cellular material or microorganisms. The system possibly takes advantage of a coupled reaction catalyzed by endogenous NMPK activity and NDPK activity according to the following reaction scheme:

AMP+D–P→D+ADP and

ADP+D–P→ATP+D wherein D–P is a high energy phosphate donor added to the cell lysate and AMP is adenosine monophosphate added to the cell lysate sample. In this reaction, ADP molecules are produced by the enzymatic transfer of a phosphate group from the high energy phosphate donor molecules (D–P) to the added AMP molecules. Then, ATP is produced by the enzymatic transfer of phosphate from D–P molecules to the ADP molecules according to the general reaction described above that is catalyzed by endogenous enzymes present in the sample.

The conversion of AMP to ATP by the endogenous enzymes, when present, can take place very rapidly, so one can detect the cell very rapidly. However, when detecting very low numbers of cells, it is preferable to obtain light reading data points after at least 10 minutes of incubation of the AMP with the endogenous enzymes. There is no negative effect resulting from incubation of the exogenously supplied AMP with the endogenous enzymes in the presence of the luciferase and luciferin.

Co-optimization of the concentrations of AMP and the high energy phosphate donors added to the samples is helpful to optimize light output from these reactions. The concentration range for the added AMP in the reaction mixture is about 0.001 mM to about 100 mM AMP. For the high energy phosphate donor, the concentration range is about 0.01 mM to about 100 mM. In preferred embodiments, the high energy phosphate donor is dCTP. Preferably, the high energy phosphate donor is provided in equal amounts or more preferably in excess relative to the concentration of adenosine phosphate acceptor. In a preferred embodiment, a reaction mixture has about 0.01 mM to about 50 mM added AMP and about 0.1 mM to about 50 mM added dCTP. In particularly preferred embodiments, addition brings the concentrations in the reaction mixture to about 0.1 mM AMP and about 1 mM dCTP.

After addition of nucleotides to the sample, the samples are incubated from 0 minutes to 3 hours, preferably incubated for about 10 to 60 minutes. The light output from the samples is determined preferably by luminescence measurement.

Other preferred buffers and reactions components can be found in the Examples.

The present invention provides important advantages over previously described cell detection systems. AMP is much more stable than ADP, and results obtained using the present invention are more reproducible than previously used methods.

As discussed above, a separate luciferase/luciferin reagent can be added before or significantly after addition of a high energy phosphate donor to the sample. Optionally, the luciferase/luciferin stock can be formulated with the high energy phosphate donor present.

E. Cellular Detection Kits

The present invention provides test kits for determining the presence of cells in a test sample. In preferred embodiments, the test kits comprise the essential reagents required for the method. In some preferred embodiments, these reagents include, but are not limited to, a high energy phosphate donor (other than ADP) which is not efficiently used by luciferase (preferably dCTP) and AMP together with luciferase and luciferin. In alternative preferred embodiments, the kit includes all these reagents with luciferase and luciferin being provided in the same solution.

In other preferred embodiments, the reagents are free of contaminating components, including, but not limited to, adenylate kinase and ATP (i.e., contaminants that can cause a false positive result).

In still other preferred embodiments, a cell treatment (permeabilization or lysis) cocktail can be provided for efficiently releasing the contents of the target cells for each of the assays intended. In some embodiments for detecting prokaryotic microorganisms, only a cationic detergent is needed. In yet other embodiments for fungal spore, yeast, or eukaryotic cells assays, a nonionic detergent reagent is included. In preferred embodiments, reagents are provided in vessels and are of a strength suitable for direct use or use after dilution. In particularly preferred embodiments, a buffer solution for diluting the cell samples can also be provided. A contemplated kit optionally includes printed instructions.

EXAMPLE 1

ATP Titration

This example demonstrates the range of ATP that can be detected when using Luciferase/Luciferin (L/L) Reagent according to manufacturer's instructions (Promega Corp., F202A) with a Turner® TD-20/20 luminometer.

A 10 mg/mL solution of ATP was prepared in nanopure water. A 1:10 serial dilution of the ATP was then prepared in 10 mM Tris, pH 7.3, to prepare ATP solutions of the following concentrations: 2 mM, 200 μM, 20 μM, 2 μM, 200 nM, 20 nM, and 2 nM.

Then, 100 μL L/L Reagent was dispensed in triplicate into luminometer tubes and 5 μL of each ATP dilution were added to the L/L reagent. The contents of the tubes were then immediately mixed and the light output measured on a Turner® TD-20/20 luminometer for 15 seconds. The following controls were also used: L/L reagent only, 10 mM Tris only, and L/L+10 μL nanopure water. The average relative light unit (rlu) values obtained are listed below.

| ATP Stock concentration | ATP final concentration | moles ATP | rlu |
|---|---|---|---|
| 2 mM | 0.95 mM | 1 × 10$^{-8}$ | >9999* |
| 200 μM | 9.5 × 10$^{-3}$ mM | 1 × 10$^{-9}$ | >9999 |
| 20 μM | 9.5 × 10$^{-4}$ mM | 1 × 10$^{-10}$ | >9999 |
| 2 μM | 9.5 × 10$^{-5}$ mM | 1 × 10$^{-11}$ | 9133 |
| 200 μM | 9.5 × 10$^{-6}$ mM | 1 × 10$^{-12}$ | 1011 |
| 20 nM | 9.5 × 10$^{-7}$ mM | 1 × 10$^{-13}$ | 94.24 |
| 2 nM | 9.5 × 10$^{-8}$ mM | 1 × 10$^{-14}$ | 9.59 |

*maximum luminometer reading

ATP concentrations between 2 nM and 2 μM can be accurately measured on a Turner® TD-20/20 luminometer.

EXAMPLE 2

AMP to ATP Conversion Using *E. coli* Cells in the Presence of Nucleotides

In this Example, *E. coli* cells placed on filters are lysed and the ability of these cells to convert added AMP and dCTP to ATP is measured.

Acetate Plus™ Filters, 0.22 micron, 13 mm (Osmonics, A025PO1300) were placed on top of 3MM Whatman™ paper cut to the same size as the filter and placed in a vacuum filtration unit. One hundred microliters of an overnight culture of JM109 *E. coli* cells (Promega Corp., P9751), grown in LB broth (10 g tryptone, 5 g yeast extract and 5 g NaCl in 1 liter water, autoclaved) were added to each of 6 filters, and the vacuum applied to pull the cells on to the filter.

One hundred microliters of Tris-buffered saline ("TBS"; 50 mM Tris-HCl [tris(hydroxymethyl)-aminomethane hydrochloride], 150 mM NaCl, pH 8.0 at 25° C.) were added to each of 6 wells in a 24 well plate. Two of the filters with the cells spotted onto them were placed into wells marked "cells only". The remaining 4 filters were washed with 50 µL of TBS while on the vacuum unit. Two of the filters were placed into wells containing TBS marked "1 wash". The remaining 2 filters were washed again with 50 µL of TBS while on the vacuum unit. Then those two filters were placed into wells containing TBS marked "2 washes".

The plate was then frozen at −20° C. until the solution was frozen, then transferred to a 37° C. water bath to thaw the solution. The freeze/thaw was repeated for a total of three cycles to lyse the cells. Then, 5 µL solution from each well were added to 45 µL water, and 5 µL of this dilution were transferred to a tube, 100 µL L/L reagent were added and the light output immediately measured on a Turner® TD-20/20 luminometer. These are "cells only" relative light unit (rlu) measurements and they are listed below.

Then 100 µL of nucleotide solution (10 mM MgCl$_2$, 5 mM dCTP, 0.1 mM AMP, 0.1×TBS) were added to each well. The plate was incubated at room temperature for 10 minutes. Then, 5 µL solution from each well were added to 45 µL water, and 2 µL of this dilution were added to 100 µL of L/L reagent and the light output immediately measured on a Turner® TD-20/20 luminometer. These are the "cell+nt/10" rlu measurements and they are listed below. The plate was permitted to further incubate at room temperature for an additional 20 minutes. Then, 5 µL of solution from each well were added to 45 µL water and 2 µL of this dilution were added to 100 µL of L/L reagent and the light output immediately measured on a Turner® TD-20/20 luminometer. These are the "cell+nucleotide/20" rlu measurements and they are listed below. All measurements were performed in duplicate and the average rlu values are listed below.

| | Relative Light Units | | |
|---|---|---|---|
| | cells only | cells + nt/10 | cells + nt/20 |
| cells only | 720 | 5225 | 3628 |
| cells/1 wash | 1000 | 4775 | 2575 |
| cells/2 washes | 828 | 4215 | 4040 |

This example demonstrates that cellular enzymes were able to convert added AMP and dCTP to ATP. Increasing the incubation time to twenty minutes lowered the amount of ATP detected.

EXAMPLE 3

Comparison of Cell Lysis with Two Extractants

In this example, two methods are compared for lysing *E. coli* cells prior to measuring the ATP content of the lysate. The example also measures the stability of the reaction over time.

JM109 *E. coli* cells were grown overnight (about 18 hours) in LB broth as described in Example 2. The overnight culture was then diluted 1:10, 1:100 and 1:1000 in LB broth. Fifty microliters of each dilution were added to 200 µL of washing/reducing agent (Celsis-Lumac, 1290142) in triplicate, incubated at room temperature for 10 seconds and combined with 100 µL of L/L reagent. The light output was then measured immediately on a Turner® TD-20/20 luminometer at 0, 2, and 5 minutes after addition of the L/L reagent. Similarly, 50 µL of each dilution were added to 200 µL of Extractant (Promega, F352A) in triplicate, incubated at room temperature for 10 seconds and combined with 100 µL of L/L reagent. The light output was then measured immediately and at 2 and 5 minutes after addition of the L/L reagent.

Control reactions containing 100 µL of L/L reagent only, 100 µL of L/L reagent+50 µL LB broth, 100 µL of L/L+200 µL Extractant, and 100 µL of L/L reagent+200 µL washing/reducing agent were also measured on a Turner® TD-20/20 luminometer, at zero, 2, and 5 minutes after addition of the L/L reagent. The relative light unit (rlu) averages are listed below.

| | | rlu |
|---|---|---|
| L/L alone | | 0.111 |
| L/L + LB broth | | 4.688 |
| L/L + Extractant | | 0.351 |
| L/L + Wash/Reduc. | | 0.394 |
| 1:10 in Wash/Reduc. | 0 min | 8828 |
| | 2 min | 8018 |
| | 5 min | 6188 |
| 1:100 in Wash/Reduc. | 0 min | 668 |
| | 2 min | 586 |
| | 5 min | 474 |
| 1:1000 in Wash/Reduc | 0 min | 85 |
| | 2 min | 74 |
| | 5 min | 64 |
| 1:10 in Extractant | 0 min | 6582 |
| | 2 min | 416 |
| | 5 min | 8.012 |
| 1:100 in Extractant | 0 min | 612.45 |
| | 2 min | 17.58 |
| | 5 min | 0.376 |
| 1:1000 in Extractant | 0 min | 70.03 |
| | 2 min | 2.93 |
| | 5 min | 0.225 |

The signal in the wash/reducing agent does not degrade as quickly over time as does the signal in the Extractant. The wash/reducing agent-treated samples also result in higher ATP levels than do the Extractant treated samples.

EXAMPLE 4

Test ATP Levels of Various Liquids Spiked with Bacteria and Permitted to Produce ATP This Example demonstrates background ATP levels in various liquids, including juices. The liquids were then spiked with bacteria and a nucleotide solution, and the resulting ATP levels in these liquids were then measured over time.

One milliliter of an overnight (about 18 hours) JM109 *E. coli* culture grown in L Broth was centrifuged at 3000 rpm for 2 minutes. The supernatant was removed and the bacterial pellet resuspended in 1 mL of fresh L Broth. Then, 100 µL of the cell suspension were separately added to 10 mL of 1×TBS, 10 mL apple juice, and 10 mL cranberry juice. The samples were then placed on ice until used. Acetate Plus™

Filters, 0.22 micron, 13 mm (Osmonics, A025PO1300) on 3MM Whatmann paper, on a vacuum filtration unit were prepared as described in Example 2. Then, 100 µL of the cell suspension in the TBS and juices were each added to a filter, in duplicate, and the vacuum applied. All the filters were then washed with 100 µL 1×TBS and the vacuum applied to pull the TBS through the filter. Control filters containing the various liquids without the bacteria were similarly prepared. Each filter was then placed in a well of a 24-well plate.

The following nucleotide solution was freshly prepared:

| | |
|---|---|
| 1 M MgCl$_2$ | 10 µL |
| 100 mM dCTP | 5 µL |
| 1 mM AMP | 1 µL |
| 10X TBS | 100 µL |
| nanopure water | 884 µL |

Then, 50 µL Extractant (Promega, F352A) was added to the well containing the first test sample. After 15 seconds, 50 µL of the nucleotide solution was added to the same well. Then, 10 µL of the solution in the well were removed and added to 100 µL of L/L reagent (Promega, F202A) and the light output measured immediately on a Turner® TD-20/20 luminometer. The extraction and nucleotide addition steps and first ATP measurement with L/L reagent were repeated with all samples. These ATP measurements were then repeated at 60 minutes and 120 minutes. The resulting average relative light units (rlu) are listed below.

| Sample | Time (min) | Average rlu |
|---|---|---|
| 1X TBS control | zero | 7.23 |
| | 60 | 9.44 |
| | 150 | 8.09 |
| 1X TBS + bacteria | zero | 11.14 |
| | 60 | 1179 |
| | 150 | 2429 |
| apple juice control | zero | 15.71 |
| | 60 | 54.92 |
| | 150 | 34.22 |
| apple juice + bacteria | zero | 40.82 |
| | 60 | 1381 |
| | 150 | 2735 |
| cranberry juice control | zero | 6.73 |
| | 60 | 10.25 |
| | 150 | 7.94 |
| cranberry juice + bacteria | zero | 12.11 |
| | 60 | 558.55 |
| | 150 | 1115 |

The data indicate the increasing levels of ATP produced over time by the lysed *E. coli* in various liquids in the presence of the nucleotide solution.

EXAMPLE 5

Determination of the Ability of the Various Reaction Solutions to Support Enzymatic ATP Synthesis In this Example, a variety of reaction solutions were tested over time to determine their ability to support enzymatic ATP synthesis.

One milliliter of an overnight (about 18 hours) JM109 *E. coli* culture in LB Broth was centrifuged to pellet the cells. The supernatant was removed and the cell pellet resuspended with 0.5 mL of 1×TBS. The cellular solution was then frozen and thawed three times to lyse the cells. The following master mix was prepared:

| | |
|---|---|
| 1 mM AMP | 60 µL |
| 100 mM dCTP | 2 µL |
| 1X TBS | 826 µL |
| 1 M MgCl$_2$ | 2 µL |

Using the above master mix, the following reaction solutions were then prepared:

| Reaction Mix | Master Mix | Extractant | 1X TBS | Celsis reagent |
|---|---|---|---|---|
| A | 15 µL | 1 mL | — | — |
| B | 15 µL | 500 µL | 500 µL | — |
| C | 15 µL | — | 1 mL | — |
| D | 15 µL | — | — | 1 mL |
| E | 15 µL | — | 500 µL | 500 µL |

The *E. coli* frozen/thawed lysate was diluted 1:10 in fresh 1×TBS. This diluted lysate and the above reaction mixes were used to prepare the following solutions:

| Solution | Reaction Mix | 1X TBS | Lysate |
|---|---|---|---|
| 1 | 190 µL A | 10 µL | — |
| 2 | 190 µL A | 10 µL | |
| 3 | 190 µL B | 10 µL | — |
| 4 | 190 µL B | 10 µL | |
| 5 | 190 µL C | 10 µL | — |
| 6 | 190 µL C | 10 µL | |
| 7 | 190 µL D | 10 µL | — |
| 8 | 190 µL D | 10 µL | |
| 9 | 190 µL E | 10 µL | — |
| 10 | 190 µL E | 10 µL | |

The above solutions were prepared one at a time and 10 µL of each reaction was immediately combined with 100 µL of L/L reagent, the light output measured on a Turner® TD-20/20 luminometer and this relative light unit value (rlu) was designated as time zero. All 10 solutions were then similarly read at time zero. Then, all tubes were similarly tested for ATP content at 30 minutes, 60 minutes, and 90 minutes after time zero. The results are listed below.

| | A1 | A2 | B1 | B2 |
|---|---|---|---|---|
| Time zero | 1.167 | 111.3 | 1.155 | 101.4 |
| 30 min | 1.279 | 128.0 | 1.647 | 149.8 |
| 60 min. | 1.335 | 195.7 | 1.313 | 186.7 |
| 90 min. | 1.141 | 222.6 | 1.306 | 217.7 |

| | C1 | C2 | D1 | D2 | E1 | E2 |
|---|---|---|---|---|---|---|
| Time zero | 1.686 | 88.7 | 0.879 | 89.91 | 0.783 | 76.54 |
| 30 min. | 2.328 | 122.5 | 1.452 | 309.2 | 1.432 | 171.1 |
| 60 min. | 1.71 | 139.9 | 1.059 | 550.7 | 0.913 | 146.0 |
| 90 min. | 1.419 | 161.1 | 1.050 | 745.7 | 1.002 | 211.8 |

EXAMPLE 6

Depletion of ATP by Luciferase Enzymatic Reaction in an *E. coli* Culture

A nucleotide mixture was prepared by combining 80 µL of 1 mM AMP (Sigma, A2002) in 20 mM Tris, pH 8.0, 8 µL 100 mM dCTP (Promega, U122A) in water with 3.92 mL TBS. An overnight (about 18 hours) culture of JM109 *E. coli* was diluted with the nucleotide mixture at dilution ratios of 1:2000, 1:10,000 and 1:50,000. Fifty microliters of TBS were added to each of 60 luminometer tubes. Then, 50 μL of each bacterial dilution described above were added to 15 of the luminometer tubes containing the TBS. As a negative control, 50 μL of nucleotide mixture were added to 15 of the luminometer tubes containing the TBS.

Then, 100 μL of L/L reagent (F120B) to which were also added AMP to a final concentration of 0.01 mM and dCTP to a final concentration of 0.1 mM, were added to all the tubes. The light output from three tubes in each set was then immediately measured in a Turner® TD-20/20 luminometer. The remainder of the tubes were incubated at room temperature and the light output, a measure of the remaining ATP levels, of three tubes in each set was measured at 15, 30, 45, and 150 minutes after the original addition of the L/L reagent. The resulting average relative light units (rlu) are listed below.

| *E. coli* Dilution | Time (min.) | Average rlu | Standard Deviation |
|---|---|---|---|
| 1:2000 | zero | 35.52 | 0.9048 |
| 1:2000 | 15 | 31.98 | 0.9140 |
| 1:2000 | 30 | 29.39 | 0.8317 |
| 1:2000 | 45 | 26.77 | 0.4940 |
| 1:2000 | 150 | 13.78 | 0.1678 |
| 1:10,000 | zero | 7.85 | 0.1157 |
| 1:10,000 | 15 | 6.93 | 0.0503 |
| 1:10,000 | 30 | 6.29 | 0.1348 |
| 1:10,000 | 45 | 5.78 | 0.1402 |
| 1:10,000 | 150 | 3.32 | 0.0700 |
| 1:50,000 | zero | 2.39 | 0.1242 |
| 1:50,000 | 15 | 2.22 | 0.1253 |
| 1:50,000 | 30 | 2.15 | 0.0817 |
| 1:50,000 | 45 | 2.04 | 0.0739 |
| 1:50,000 | 150 | 1.62 | 0.0883 |

EXAMPLE 7

Apple Juice Spiked with *E. coli* and Filtered Prior to ATP Synthesis and Detection A master mix solution was prepared by combining the following:

| 100 mM dCTP | 10 μL1 |
|---|---|
| 1 mM AMP | 10 μL |
| 1 M MgCl$_2$ | 10 μL |
| Nanopure water | 70 μL |

The master mix solution was placed on ice until use. Ten milliliters of freshly opened apple juice was added to each of 6 tubes. Each tube was inoculated with 10 μL of an overnight culture of JM109 cells and mixed by inverting. The solutions were each filtered through a separate sterile Acrodisc® 13—0.2 μm filter on a vacuum manifold. In addition, an un-inoculated 10 mL sample of apple juice was filtered to serve as a negative control.

The control filters and two of the sample filters were washed twice with 1 mL of TBS. Two of the sample filters were washed once with 1 mL of TBS and two of the sample filters were not washed. Then 1 mL Extractant (Promega, F352A) was then slowly pushed through each filter and captured in a separate 1.5 mL tube, followed by air being pushed through the filter and any residual fluid on the filter captured in the same 1.5 mL tube.

Twenty microliters from each tube was added to 200 μl L/L reagent and the light output measured immediately with a Turner TD-20/20 luminometer. Then 2 μL of the master mix solution was added to each of the samples containing the L/L reagent and the light output was again measured every 15 minutes for a total of one hour. As an additional control 10 μL of the overnight bacterial culture was added to 200 μL Extractant. The relative light unit values are listed below.

| Sample | Relative Light Units | | | | |
|---|---|---|---|---|---|
| | No NT | 0 min | 15 min | 30 min | 60 min |
| No Cell Control* | 0.064 | 0.070 | 0.091 | 0.127 | 0.027 |
| No Cell Control | 0.078 | 0.036 | 0.041 | 0.134 | 0.053 |
| No wash sample | 0.215 | 0.403 | 0.407 | 0.525 | 0.851 |
| No wash sample | 0.170 | 0.454 | 0.440 | 0.695 | 0.477 |
| One wash sample | 0.030 | 0.049 | 0.160 | 0.179 | 0.164 |
| One wash sample | 0.086 | 0.201 | 0.243 | 0.473 | 0.160 |
| Two wash sample | 0.088 | 0.137 | 0.158 | 0.299 | 0.163 |
| Two wash sample | 0.074 | 0.129 | 0.055 | 0.277 | 0.236 |
| cells direct | 20.31 | 49.43 | 61.88 | 63.24 | 62.16 |
| cells direct | 23.26 | 35.19 | 44.76 | 47.24 | 43.96 |

*10 μL master mix used

EXAMPLE 8

Filtration and ATP Amplification of Large Volume Samples

One milliliter of an overnight (about 18 hours) culture of *E. coli* JM109 in LB Broth was added to each of six 100 mL samples of sterile 1×TBS. Each sample was passed through a 0.22 μm Millipore® Express Membrane filter (Millipore, SCGPUOIRE). Four of the six samples were washed with 10 mL of sterile 1×TBS. Two of these four samples were further washed with an additional 10 mL of sterile 1×TBS.

Then, 2 mL of extractant (Promega, F352A) were added to each of the six filters. The extractant was permitted to sit on the filter for 15 seconds before applying the vacuum and collecting the extractant that passed through the filter. The filters were then cut with a razor so they each would fit into a well of a 6-well microtiter plate. Two milliliters of extractant were then added to each well and mixed. Thereafter, 20 μL from each well were combined with 100 μL of L/L reagent (Promega, F202A) and the light output measured immediately with a Turner® TD-20/20 luminometer (Time 0).

A master mix solution containing dCTP and AMP was prepared as described in Example 7. The master mix solution (30 μL) was added to each sample. The samples were incubated for 30 minutes at room temperature. Then, 20 μL of each sample were combined with 100 μL of L/L reagent and the light output measured immediately with a Turner® TD-20/20 luminometer. An additional reading was taken 90 minutes after addition of the master mix solution. The relative light unit values are listed below.

| | Filter +<br>extractant +<br>no master mix | Filter +<br>extractant +<br>master mix | |
|---|---|---|---|
| Sample | 0 min. | 30 min. | 90 min. |
| no wash | 394 | 1823 | 2446 |
| no wash | 337.8 | 1107 | 1581 |
| 1 wash | 636.4 | 2783 | 3553 |
| 1 wash | 472.2 | 2041 | 2461 |
| 2 washes | 667.4 | 2285 | 2733 |
| 2 washes | 427.9 | 1457 | 1787 |

EXAMPLE 9

Filtration and ATP Amplification of Large Volume Samples of Juices

Two milliliters of an overnight (about 18 hours) culture of JM109 *E. coli* cells were placed into 50 mL of fresh LB broth and further incubated in a 37° C. shaker for two hours. Four hundred milliliters of apple juice were filter-sterilized. Fifty milliliters of the sterilized apple juice were inoculated with 100 $\mu$L of the JM109 culture. A 1:10 serial dilution of this apple juice/JM109 solution was prepared in apple juice. Each resulting sample was then filtered in a Nalgene® 150 mL filter unit (0.2 $\mu$m, nylon).

The filters were removed from the filtration unit, cut into pieces and each placed into a well of a 6 well plate. One milliliter of Extractant (Promega, F352A) was added to each well and mixed. Twenty microliters from each well were added to 100 $\mu$L of L/L reagent and the light output measured immediately using a Turner® TD-20/20 luminometer. Then, 10 $\mu$L of master mix solution, prepared as described in Example 7, were added to each well and the plate was incubated for 60 minutes at room temperature.

At 30 minutes and at 60 minutes, 20 $\mu$L from each well were added to 100 $\mu$L of L/L reagent and the light output measured immediately using a Turner® TD-20/20 luminometer. The resulting relative light units are listed below. One hundred microliters from each well were spread onto an LB agar plate and incubated overnight (about 18 hours) at 37° C. None of these plates showed any bacterial growth, indicating the innoculated bacteria had all been lysed.

| Sample | 0 min | 30 min | 60 min |
|---|---|---|---|
| Initial sample | 246.9 | 655.1 | 741.5 |
| $10^{-1}$ dilution | 10.75 | 5.212 | 8.399 |
| $10^{-2}$ dilution | 1.565 | 3.065 | 3.853 |
| $10^{-3}$ dilution | 1.089 | 2.379 | 2.656 |
| $10^{-4}$ dilution | 1.635 | 4.177 | 4.821 |
| $10^{-5}$ dilution | 1.985 | 3.903 | 5.590 |
| $10^{-6}$ dilution | 0.699 | 1.599 | 2.687 |
| no bacteria control | 1.143 | 2.524 | 2.554 |

EXAMPLE 10

Test ATP Amplification of Apple Juice Samples Inoculated with Varying Volume of Bacteria and Filtered The filtration units (Millipore® SX0001300) used in this Example were assembled with 13 mm 0.45 $\mu$m Corning® filters (Corning 140418) and Millipore® O-rings (SX0001301).

A 1:10 serial dilution of filter-sterilized apple juice initially combined 1:1 with an overnight culture of JM109 *E. coli* bacteria was prepared using apple juice as the diluent.

A master mix solution was prepared by combining the following:

| 100 mM dCTP | 25 $\mu$L |
|---|---|
| 1 mM AMP | 125 $\mu$L |
| 1 M MgCl$_2$ | 125 $\mu$L |
| Nanopure water | 2230 $\mu$L |

Twenty milliliters of filtered apple juice were added to each of eighteen 50 mL conical tubes. To sets of three tubes were added the following volumes of the 1:10,000 dilution of bacteria in apple juice: 200, 400, 600, 800, and 1000 $\mu$L. A set of control tubes had no bacterial culture added.

The contents of each of the tubes were passed through separate filtration units as described above. Each filter was then washed twice with 2 mL TBS. The filters were removed from the filtration units and each placed into a well of a 24 well plate.

Then, 100 $\mu$L of Extractant was added to each well containing a filter. The samples were permitted to incubate for 4 minutes at room temperature. Then, 100 $\mu$L of master mix solution was added to each well and the plate was rocked to mix. At 0, 19 and 180 minutes after addition of the master mix, 25 $\mu$L were removed from each well, placed in a separate luminometer tube with 100 $\mu$L of L/L reagent and the light output measured immediately on a Turner® TD-20/20 luminometer. The resulting relative light unit values are listed below.

| Sample | 0 min | 90 min | 180 min |
|---|---|---|---|
| Control | 18.00 | 30.31 | 12.98 |
| | 18.06 | 26.18 | 17.02 |
| | 24.36 | 42.86 | 45.34 |
| Ave: | 20.14 | 33.12 | 25.11 |
| 200 $\mu$L cells | 11.33 | 16.69 | 16.51 |
| | 8.355 | 11.53 | 11.41 |
| | 34.52 | 62.35 | 66.58 |
| Ave: | 18.07 | 30.19 | 31.5 |
| 400 $\mu$L cells | 14.17 | 26.26 | 26.38 |
| | 7.108 | 9.431 | 10.47 |
| | 14.38 | 48.23 | 49.30 |
| Ave: | 11.89 | 27.97 | 28.72 |
| 600 $\mu$L cells | 14.06 | 9.387 | 20.77 |
| | 16.19 | 37.36 | 40.31 |
| | 14.33 | 25.78 | 25.67 |
| Ave: | 14.86 | 24.18 | 28.92 |
| 800 $\mu$L cells | 26.4 | 41.75 | 44.50 |
| | 10.39 | 15.34 | 20.70 |
| | 11.80 | 19.53 | 21.05 |
| Ave | 16.34 | 25.54 | 28.75 |
| 1000 $\mu$L cells | 14.62 | 29.39 | 31.94 |
| | 44.31 | 132.5 | 144.2 |
| | 15.35 | 32.28 | 36.77 |
| Ave: | 24.76 | 64.72 | 70.97 |

EXAMPLE 11

ATP Increase in Bacterial Cell Lysate Supplied AMP and dCTP

As shown in Example 3, the presence of the Extractant (Promega, F352A) causes the signal of the luciferase reaction to decrease rapidly over time. It has been found that addition of Tritone® N-101 (Sigma) to the L/L reagent at a concentration of 0.1% in the assay eliminates this effect. The presence of the Triton® N-101 also acts to lyse the cells. In this Example, bacteria were added to different assay reagents and light output was read at several time points. It was determined that the luciferase signal derived from lysed bacterial cells can be increased over time by the addition of dCTP and AMP. The bacterial enzymes are used to convert AMP to ATP using dCTP as a high energy phosphate donor.

Fresh L/L reagent was prepared by combining the components listed in the table below, then making up the final volume to 5 mL with water.

| Component | Volume | Final Conc. (2X L/L) |
|---|---|---|
| 10 mM Luciferin (JBL, 1300A) | 100 µL | 200 µM |
| 1 M MgSO₄ | 80 µL | 16 µM |
| 0.5 M EDTA | 2 µL | 0.2 mM |
| 1% gelatin | 1 mL | 0.2% |
| 3 mg/mL Luciferase (Luc90-1B5) | 33 µL | 20 µg/mL |
| 10% Triton N-101 | 100 µL | 0.2% |
| 80% glycerol | 625 µL | 10% |
| 5 M NaCl | 20 µL | 20 mM |
| 1 M Hepes | 500 µL | 100 mM |

The following six different assay reagents were prepared. When dCTP and AMP were present, they were at a final concentration of 2 mM. When Extractant was present, 300 µL of Extractant were added per 1000 µL total volume.

1. 1×L/L
2. 1×L/L+dCTP
3. 1×L/L+dCTP+AMP
4. 1×L/L+Extractant
5. 1×L/L+dCTP+Extractant
6. 1×L/L+dCTP+AMP+Extractant One milliliter of an overnight (about 18 hours) culture of JM109 *E. coli* cells was centrifuged to pellet the cells. The cells were washed twice with 1×TBS (10×is 100 mM Tris, 150 mM NaCl, pH 7.5) and then diluted 1:100 in 1×TBS. Ten microliters of the diluted bacteria were plated on a LB agar plate, incubated overnight at 37° C. and 476 colonies resulted. This indicates that 476 cells were present in a 10 µL sample of the 1:100 dilution.

Ten microliters of the diluted bacteria were added to 100 µL of each of the six L/L assay reagents listed above. Light output was measured immediately and then again at 5, 35, and 85 minutes after the addition of the L/L assay reagents. A Turner® TD-20/E luminometer was used. The average relative light unit values obtained minus the background values for each assay reagent without bacteria present are listed below.

| | Average rlu | | |
|---|---|---|---|
| Time | L/L | L/L + dCTP | L/L + dCTP + AMP |
| 0 min | 1569.19 | 1560.22 | 64.28 |
| 5 min | 394.50 | 1265.42 | 146.52 |
| 35 min | 38.17 | 769.57 | 896.93 |
| 84 min | 26.02 | 672.70 | 3230.36 |

| | Average rlu | | |
|---|---|---|---|
| Time | L/L + Ext | L/L + dCTP + Ext | L/L + dCTP + AMP + Ext |
| 0 min | 920.38 | 1334.29 | 38.82 |
| 5 min | 300.05 | 1171.80 | 61.71 |
| 35 min | 38.17 | 769.57 | 896.93 |
| 84 min | 44.66 | 515.58 | 1920.78 |

Triton® N-101 in the L/L was sufficient to cause lysis of the bacteria. Only when both dCTP and AMP were present in the assay did the relative light unit values increase over time. The samples containing dCTP and AMP, but no Extractant resulted in higher values indicating the possibility that the Extractant has an inhibiting component.

EXAMPLE 12

Addition of Triton N-101 to L/L Reagent

As demonstrated in Example 3, the presence of the extractant causes rapid decrease of light output in an assay measuring ATP with luciferase. In this Example, various concentrations of Triton N-101 are tested along with various concentrations of chlorhexidine to determine whether these variables affect the signal stability resulting from luciferase enzyme activity in the extractant over time. Signal stability is the ability to maintain luminescent signal over a period of time of about three minutes. The enzyme itself (90-1B5 and larger numbers in the name of the mutant) are known to be very stable in extractant. If the enzyme is incubated with extractant for three hours at both RT and at 50° C. and aliquots are removed at different time points and assayed for luminescence, very little activity is lost after three hours. However, the wild type LucPpy luciferase has low enzyme stability in extractant.

Three types of 2×L/L reagent were prepared as described in Example 11 with the exception that Triton N-101 detergent was either not present, or present at a final concentration of 1 or 2 percent. In addition, solutions of chlorhexidine were prepared in 50 mM Hepes, pH 7.8 to final concentrations of 0, 0.1, 0.3, 0.5, 1, 1.5, and 3 percent. Normal extractant (Promega, F352A) alone was also tested. To test, 150 µL 0.023 µM ATP in 50 mM Hepes pH 7.8 was combined with 100 µL extractant and 100 µL 2×L/L reagent. Each of the three types of 2×L/L reagents were similarly tested. The light output was then immediately measured in a Turner TD-20/E luminometer. The resulting relative light values are listed below.

| Sample | Relative light value |
|---|---|
| NO TRITON L/L | |
| % chlorhexidine 0 | 1 | 1096 |
| 0.1 | 2 | 1198 |
| 0.3 | 3 | 1215 |
| 0.5 | 4 | 1084 |
| 1 | 5 | 666 |
| 1.5 | 6 | 34 |
| ext | 7 | 511.5 |
| 1% TRITON L/L | |
| % chlorhexidine 0 | 1 | 1013 |
| 0.1 | 2 | 964 |
| 0.3 | 3 | 749 |
| 0.5 | 4 | 605.5 |
| 1 | 5 | 298.3 |
| 1.5 | 6 | 118.6 |
| ext | 7 | 741.8 |
| 2% TRITON L/L | |
| % chlorhexidine 0 | 1 | 991 |
| 0.1 | 2 | 915 |
| 0.3 | 3 | 700 |
| 0.5 | 4 | 593.5 |
| 1 | 5 | 268.3 |
| 1.5 | 6 | 173.8 |
| ext | 7 | 649 |
| NO TRITON | |
| 0 | 1 | 1018 |
| 0.1 | 2 | 1218 |
| 0.3 | 3 | 1118 |
| 0.5 | 4 | 1076 |
| 1 | 5 | 540.3 |
| 1.5 | 6 | 18.21 |
| ext | 7 | 541.5 |

It was determined from the data that the addition of Triton N-101 to the L/L reagent greatly reduces the deleterious affects of both the extractant and the high concentration of chlorhexidine. There is approximately a 30 percent loss in activity when extractant is used when compared to water.

EXAMPLE 13

Comparison of LucPpy Luciferase and Luc90-1B5 Luciferase in an ATP Conversion Assay In this example, dCTP and AMP are added to lysed bacterial cells under the theory that bacterial enzymes will perform a phosphate transfer from the dCTP to the AMP to form ATP. The resulting ATP was then measured with two types of luciferase, LucPpy and Luc90-1B5. The Luc90-1B5 luciferase is a thermostable luciferase (Promega).

JM109 bacterial cells were grown overnight in LB broth and stored at 4° C. This culture was diluted 1:10 in fresh LB broth and grown for one hour. Four milliliters of this diluted cell culture were centrifuged to pellet the cells and the cells resuspended in 4 mL TBS. Two milliliters of the cell suspension were combined with 2 mL TBS and the other 2 mL of the cell suspension were combined with 2 mL lysis reagent (25 mM Tris phosphate pH 7.8, 2 mM DTT, 2 mM CTDA (Sigma), 10 percent glycerol and 1 percent Triton X-100; Promega Corp.#E1531) containing 1.25 mg/mL lysozyme. The cell solutions were then allowed to incubate at room temperature for 15 minutes during which the solutions containing CCLR (Promega Corp.) would lyse the cells and the solutions containing TBS would not lyse the cells. The following three substrates, dCTP, dCTP+AMP, ATP, were prepared:

| | dCTP | dCTP + AMP | ATP |
|---|---|---|---|
| 100 μM dCTP | 50 μL | 50 μL | — |
| 100 μM AMP | — | 50 μL | — |
| 1 M MgSO$_4$ | 50 μL | 50 μL | 50 μL |
| 100 μM ATP | — | — | 50 μL |
| water | 900 μL | 850 μL | 900 μL |

Samples were then prepared containing 500 μL bacteria or bacterial lysate, 20 μL substrate, and 480 μL water. The samples were incubated at 37° C., aliquots were removed at different time points and then placed on ice. Ten microliters of each sample was then combined with 100 μL L/L assay reagent (100 μM luciferin, 50 mM Hepes pH 7.8, 8 mM MGSO$_4$, 0.1 percent gelatin, 0.1 mM EDTA, 0.2 μg/mL luciferase) and the light output measured. Each sample type was measured in triplicate. The relative light values obtained are listed below.

| | Relative Light Units | |
|---|---|---|
| Time | Luc90-1B5 Luciferase | LucPpy Luciferase |
| LYSED CELLS/dCTP | | |
| 0 | 170.2 | 59.18 |
| 10 | 171.53 | 59.79 |
| 20 | 168.27 | 58.45 |
| 40 | 158.5 | 54.89 |
| LYSED CELLS/dCTP + AMP | | |
| 0 | 88.67 | 78.56 |
| 10 | 123.5 | 110.57 |
| 20 | 171.13 | 158.23 |
| 40 | 287.2 | 259.34 |
| LYSED CELLS/ATP | | |
| 0 | 543.6 | 181.34 |
| 10 | 435.97 | 142.47 |
| 20 | 314.87 | 101.77 |
| 40 | 184.07 | 59.43 |
| UNLYSED CELLS/dCTP | | |
| 0 | 132.37 | 40.75 |
| 10 | 154.33 | 46.18 |
| 20 | 160.37 | 48.73 |
| 40 | 137.23 | 41.21 |
| UNLYSED CELLS/dCTP + AMP | | |
| 0 | 136.53 | 109.567 |
| 10 | 150.13 | 121.4 |
| 20 | 142.63 | 113.97 |
| 40 | 118.7 | 93.7 |
| UNLYSED CELLS/ATP | | |
| 0 | 652.4 | 189.27 |
| 10 | 642.73 | 186.97 |
| 20 | 621.93 | 180.63 |
| 40 | 604.53 | 172.967 |

The increase in light output signal that is seen with the addition of AMP and dCTP to the lysed cells is not seen for the unlysed cells. This shows that this process is dependent upon cell lysis.

When a sample of either lysed or unlysed cells is incubated with a spike of ATP, there is a decrease in light output over time. The decrease is much more rapid in the samples that had been lysed. This could be due to components in the lysis buffer that are degrading the ATP or components in the lysed cells that were released and are now available to degrade the ATP. There was equivalent signal increase with both of the luciferases used to detect the ATP produced in the lysed cells containing added AMP and dCTP.

EXAMPLE 14

Effect of Additives on Luminescence Over Time

This example determined the effect of additives on luminescence over a 50 minute time period in an all-in-one assay where the extractant was the lysis buffer, CCLR. The thermostable Ppe2 luciferase, 90-1B5, was used in this experiment. A JM109 culture was grown in LB broth overnight, shaking at 37° C. The cells were then washed twice in TBS and the washed cells were diluted 1:10 in TBS. Apyrase (2 units), and 10 µL 1 M MgSO₄ were added to 1 mL of the diluted cells. The cells were then incubated for 10 minutes at room temperature. Assay reagent (2×L/L) was prepared according to the following table.

| | |
|---|---|
| 10 mM luciferin | 100 µL |
| 1 M MgSO₄ | 80 µL |
| 1 M Hepes | 500 µL |
| 0.5 M EDTA | 2 µL |
| 1 percent gelatin | 1 mL |
| Luc90-1B5 luciferase (3 µg/µL) | 3.3 µL |
| 5 M NaCl | 20 µL |
| water to final volume of 5 mL | |

Three types of L/L reagent were prepared as follows.

a) L/L
   500 µL 2×L/L+500 µL water
b) L/L+dCTP
   500 µL 2×L/L+10 µL 100 mM dCTP+490 µL water
c) L/L+AMP+dCTP
   500 µL 2×L/L+10 µL 100 mM dCTP+10 µL 10 mM AMP+480 µL water The apyrase-treated cells (45 µL) were combined with Buffer A (325 mM K₂HPO₄, 6.5 mM CDTA, 0.1% Triton X-100). The cells were then frozen at −70° C. and then thawed. Next, CCLR lysis buffer ((175 µL; 25 mM Tris phosphate pH 7.8, 2 mM DTT, 2 mM CTDA, 10 percent glycerol and 1 percent Triton X-100) containing lysozyme 1.25 µg/µL) was added and the cells were incubated at room temperature for 20 minutes to lyse the cells. In a separate tube, apyrase-treated cells (45 µL) were combined with TBS (195 µL of a 1×stock) to make the unlysed cell control. Both tubes of cells were further diluted 1:100 into 1×TBS and they were then prepared for assay. An ATP control (0.01 mM ATP) was also assembled.

The lysed and the unlysed cells were each combined with the different L/L reagents and read several times over a 50 minute timespan. Each L/L reagent was also measured alone to determine how the background varied with time. Other controls were prepared and are listed in the table below. The relative light units were measured in a Turner TD-20/E luminometer, with each reaction read at 6 different times. The relative light unit measurements are listed below.

| time (min.) | L/L + cells | L/L + lysate | L/L + dCTP + cells | L/L + dCTP + lysate |
|---|---|---|---|---|
| 0 | 135.1 | 22.7 | 183.4 | 116.6 |
| 13 | 76 | 13.4 | 172.9 | 127.5 |
| 21 | 39.7 | 7.05 | 156.7 | 135.8 |
| 30 | 26.8 | 4.5 | 147.9 | 140.7 |
| 40 | 15.5 | 2.4 | 136.8 | 145.3 |
| 50 | 8.1 | 1.3 | 122.2 | 147.4 |

| time (min.) | L/L | L/L + dCTP | L/L + dCTP + AMP | L/L + dCTP + AMP + cells | L/L + dCTP + AMP + lysate |
|---|---|---|---|---|---|
| 0 | 35.57 | 140.78 | 5.79 | 7.2 | 7.2 |
| 13 | 24.11 | 138.08 | 5.89 | 9.7 | 38.7 |
| 21 | 18.93 | 127.33 | 5.93 | 12.8 | 84.63 |
| 30 | 15.01 | 120.50 | 6.23 | 14.4 | 114.8 |
| 40 | 11.75 | 110.97 | 6.12 | 17 | 151.7 |
| 50 | 8.62 | 100.35 | 6.02 | 20.3 | 197.3 |

| time (min.) | L/L + ATP | L/L + dCTP + ATP | L/L + ATP + cells | L/L + ATP + lysis buffer | L/L + ATP + lysate |
|---|---|---|---|---|---|
| 0 | 7597.7 | 2773.42 | 6199.1 | 5846.8 | 5988.7 |
| 13 | 4910.39 | 2600.39 | 2678.85 | 4619.09 | 3212.57 |
| 21 | 3887.18 | 2351.91 | 1622.75 | 3848.03 | 1904.42 |
| 30 | 3027.72 | 2215.9 | 945.89 | 3168.24 | 1045.54 |
| 40 | 2384.65 | 2032.43 | 532.21 | 2632.28 | 547.54 |
| 50 | 1805.88 | 1822.17 | 277.33 | 2099.22 | 249.78 |

The presence of dCTP tends to decrease the luminescence in samples L/L provided with an ATP spike. When AMP is added, the light output is further decreased. For light output to increase over time, both AMP and dCTP must be provided to a cell lysate. The components of the lysis buffer do not affect the luminescence.

EXAMPLE 15

Various Lysis Reagents Tested for the Ability to Enhance ATP Generation from dCTP and AMP in the Presence of Bacteria The effect of cell lysing reagents, chlorhexidine and polymixin B sulfate, on the conversion of AMP and dCTP to ATP was examined in this Example. Fresh 2×L/L reagent was prepared according to the following table.

| | |
|---|---|
| 10 mM luciferin | 60 µL |
| 1 M MgSO₄ | 96 µL |
| 1 M Hepes pH 7.8 | 600 µL |
| 1 percent gelatin | 1.2 mL |
| 0.3 mg/mL Luc90-1B5 luciferase enzyme | 40 µL |

The four following L/L assay reagents were assembled using the 2×L/L reagent described above.

1×L/L reagent with 0.05 percent chlorhexidine
1×L/L reagent with 0.05 percent chlorhexidine and 100 µL 10 mg/mL Polymixin B Sulfate
1×L/L reagent with 0.075 percent chlorhexidine
1×L/L reagent with 1×CCLR The four types of L/L reagents were divided into two 450 µL aliquots. To one aliquot, nothing was added. To the other aliquot was added dCTP nucleotide (1 µL of 100 mM dCTP)

and AMP nucleotide (1 μL of 10 mM AMP). An overnight culture of JM109 cells (6 mL) was washed three times in TBS and the final cell pellet was resuspended in TBS (1.5 mL). Ten microliters of the cell solution was then added to each of the five L/L assay reagents with no added nucleotide and those with added dCTP and AMP. The resulting light output was measured immediately in a Turner TD-20/E luminometer. Control reactions containing no cells were similarly tested. The average relative light unit values are listed below. Samples with polymixin B sulfate and chlorhexidine yielded the most light and the rate of ATP production was increased in these samples.

| NO ADDED NUCLEOTIDES | | | | |
|---|---|---|---|---|
| time (min.) | 0.05% chlorhex | 0.5% chlorhex + PMB | 0.075% chlorhex | 1XCCLR |
| 0 | 74.306 | 206.121 | 61.651 | 91.809 |
| 16.848 | 109.159 | 178.598 | 102.403 | 90.608 |
| 55.398 | 53.167 | 100.524 | 52.114 | 69.058 |
| 126.18 | 16.879 | 37.567 | 17.267 | 43.873 |
| ADDED NUCLEOTIDES | | | | |
| time (min.) | 0.05% chlorhex | 0.05% chlorhex + PMB | 0.075% chlorhex | 1XCCLR |
| 0 | 20.529 | 48.954 | 33.453 | 67.798 |
| 16.848 | 192.896 | 238.294 | 254.199 | 94.243 |
| 55.398 | 433.382 | 846.712 | 597.81 | 153.721 |
| 126.18 | 636.183 | 2070.853 | 976.443 | 231.428 |

EXAMPLE 16

Titration of Both AMP and dCTP to Optimize Conditions for Single Cell Detection LB broth was inoculated with JM109 cells and incubated at 37C for three hours with shaking. The cells were then pelleted and washed three times in 1×TBS. The cell solution was then diluted 1:10, 1:100, and 1:1000 and 10 μL aliquots of each were spread onto LB plates and incubated overnight. It was found that about 50,000 cells were contained in the 10 μL from the 1:10 dilution. The following 2×L/L reagent was made:

| | |
|---|---|
| 10 mM luciferin | 50 μL |
| 1M MgSO$_4$ | 80 μL |
| 1M Hepes, pH 7.8 | 500 μL |
| 1 percent gelatin | 500 μL |
| Luc90-1B5 luciferase (3 mg/ml) | 2 μL (2 ng) |
| water added to final volume of 5 mL | |

The following 10×nucleotide mixes were prepared in water to a final volume of 1 milliliter.

| Soln Final Concentration | | 100 mM dCTP | 10 mM AMP |
|---|---|---|---|
| 1 | 0.1 mM dCTP 0.01 mM AMP | 1 μL | 1 μL |
| 2 | 1 mM dCTP 0.01 mM AMP | 10 μL | 1 μL |
| 3 | 10 mM dCTP 0.01 mM AMP | 100 μL | 1 μL |

| Soln Final Concentration | | 100 mM dCTP | 10 mM AMP |
|---|---|---|---|
| 4 | 0.1 mM dCTP 0.1 mM AMP | 1 μL | 10 μL |
| 5 | 1 mM dCTP 0.1 mM AMP | 10 μL | 10 μL |
| 6 | 10 mM dCTP 0.1 mM AMP | 100 μL | 10 μL |
| 7 | 0.1 mM dCTP 1 mM AMP | 1 μL | 100 μL |
| 8 | 1.0 mM dCTP 1 mM AMP | 10 μL | 100 μL |
| 9 | 10 mM dCTP 1 mM AMP | 100 μL | 100 μL |

The final L/L assay reagents contained:

| | |
|---|---|
| 2× L/L reagent | 500 μL |
| water | 300 μL |
| Polymixin B Sulfate (1 mg/mL) | 100 μL |
| 10× nucleotide mix | 100 μL |
| 20% chlorhexidine (add last) | 2.5 μL |

Ten microliters (50,000, 5000, 500, 0 cells) of the diluted cells were added to 100 μL of the L/L assay reagent. Each sample type was read four times over the course of 91 minutes. The light output was measured with a Turner TD-20/E luminometer and the relative light unit values are listed below.

| time (min) | 0.01 mM dCTP 0.001 mM AMP | 0.1 mM dCTP 0.001 mM AMP | 1 mM dCTP, 0.001 mM AMP |
|---|---|---|---|
| 0 | 878.532 | 834.598 | 645.933 |
| 18 | 1756.38 | 2161.73 | 2865.73 |
| 49 | 2332.63 | 3042.08 | 6494.63 |
| 91 | 2461.71 | 3533.68 | 10503.6 |

| time (min) | 0.01 mM dCTP 0.01 mM AMP | 0.1 mM dCTP 0.01 mM AMP | 1 mM dCTP 0.01 mM AMP |
|---|---|---|---|
| 0 | 781.71 | 740.994 | 653.003 |
| 18 | 1717.63 | 2083.92 | 2733.67 |
| 49 | 2304.46 | 2968.73 | 5953.45 |
| 91 | 2479.09 | 3509.54 | 9580.26 |

| time (min) | 0.01 mM dCTP, 0.1 mM AMP | 0.1 mM dCTP, 0.1 mM AMP | 1 mM dCTP, 0.1 mM AMP |
|---|---|---|---|
| 0 | 150.942 | 151.264 | 200.958 |
| 18 | 2122.67 | 13724.3 | 21784.8 |
| 49 | 5659.08 | 27256.1 | 48226.5 |
| 91 | 8246.38 | 32550 | 66430.6 |

The data demonstrate that the highest concentration of both dCTP and AMP tested gave the greatest light output yield over time.

EXAMPLE 17

Alternate Nucleotides as Source for Phosphate Transfer Group

In this example, UTP (uracil triphosphate) and dITP (deoxyinosine triphosphate) are compared to dCTP as a source for the phosphate group that is transferred to AMP by the action of bacterial enzymes in a bacterial cell lysate. This transfer results in the formation of ATP that can be acted upon by luciferase, in the presence of luciferin and Mg++, to produce light.

The 2×L/L reagent as described in Example 16 was freshly prepared and used to prepare fresh 1×L/L assay reagent containing polymixin B sulfate, chlorohexidine, and nucleotides, also as described in Example 16. However, the 10×nucleotide compositions used in the preparation of the 1×L/L reagent are as follows for a 10×nucleotide solution of 1 mL total volume:

| Solution | Final Conc. (1×) | In one milliliter 10× Solution | |
|---|---|---|---|
| | | 100 mM dCTP ($\mu$L) | 10 mM AMP ($\mu$L) |
| 1. | no nucleotides | zero | zero |
| 2. | 1 mM dCTP, 0.1 mM AMP | 10 | 10 |
| 3. | 1 mM dCTP, 0.3 mM AMP | 10 | 30 |
| 4. | 1 mM dCTP, 1 mM AMP | 10 | 100 |
| | | 10 mM UTP ($\mu$L) | 10 mM AMP ($\mu$L) |
| 5. | 1 mM UTP, 0.1 mM AMP | 100 | 10 |
| 6. | 1 mM UTP, 0.3 mM AMP | 100 | 30 |
| 7. | 1 mM UTP, 1 mM AMP | 100 | 100 |
| | | 5 mM dITP ($\mu$L) | 10 mM AMP ($\mu$L) |
| 8. | 0.1 mM dITP, 0.1 mM AMP | 20 | 10 |
| 9. | 0.1 mM dITP, 0.3 mM AMP | 20 | 30 |
| 10. | 0.1 mM dITP, 1 mM AMP | 20 | 100 |

JM109 *E. coli* cell dilutions were prepared as described in Example 16. Ten microliters of a $1 \times 10^{-4}$ dilution resulted in 225 colonies, indicating the presence of 225 cells in the 10 $\mu$L volume. Ten microliters of the cells (22,500, 2250, and 225 cells) were added to 100 $\mu$L of the various 1×L/L assay reagents. The light output was read in a Turner® TD-20/E luminometer at 0, 20, 40, and 70 minutes after the L/L assay reagent was added. The resulting net relative light unit (rlu) values for the 2250 cell data points are listed below.

The 0.1 mM concentration of AMP provided the highest rate of ATP generation. The other nucleotides tested, UTP and dITP, can substitute for dCTP as the high energy phosphate donor.

EXAMPLE 18

Nucleotide Concentration Optimization Permits Detection of 23 Cells

In this example, the nucleotide concentration was further optimized, and a combination of UTP and dCTP was tested to determine if they had an additive effect. The following 2×L/L assay reagent was freshly prepared:

| | |
|---|---|
| 10 mM luciferin | 50 $\mu$L |
| 1M MgSO$_4$ | 80 $\mu$L |
| 1M Hepes, pH 7.8 | 500 $\mu$L |
| 1% gelatin | 500 $\mu$L |
| 0.3 mg/mL 90-1B5 luciferase (Promega) | 20 $\mu$L |
| Water to a final volume of 5 mL | |

The following 10×Nucleotide solutions were prepared in water to a final 1 mL volume:

1. no nucleotides
2. 10 mM dCTP, 3 mM AMP
3. 10 mM dCTP, 0.5 mM AMP
4. 10 mM dCTP, 1 mM AMP
5. 5 mM dCTP, 5 mM UTP, 0.3 mM AMP
6. 5 mM dCTP, 5 mM UTP, 0.5 mM AMP
7. 5 mM dCTP, 5 mM UTP, 1 mM AMP
8. 10 mM UTP, 0.3 mM AMP
9. 10 mM UTP, 0.5 mM AMP
10. 10 mM UTP, 1 mM AMP The various 1×L/L assay reagents were prepared by combining the following:

500 $\mu$L 2×L/L
100 $\mu$L 10 $\mu$L/mL Polymixin B Sulfate
2.5 $\mu$L 20% chlorhexidine
100 $\mu$L 10×nucleotide solution
water to a final of 1 mL Fifty microliters of JM109 cells were inoculated into 50 mL of LB Broth and grown for 2 hours and 40 minutes shaking at 37° C. The cells were washed twice in TBS and diluted in TBS to $1 \times 10^{-3}$, $1 \times 10^{-4}$, and $1 \times 10^{-5}$. Ten microliters of each dilution were plated on a LB agar plate and

| time | 1 mM dCTP, 0.1 mM AMP | 1 mM dCTP, 0.3 mM AMP | 1 mM dCTP, 1 mM AMP | 1 mM UTP, 0.1 mM AMP | 1 mM UTP, 0.3 mM AMP |
|---|---|---|---|---|---|
| 0 | 21.764 | 12.595 | 7.968 | 86.278 | 33.966 |
| 20 | 268.951 | 99.541 | 34.712 | 379.085 | 160.365 |
| 40 | 554.125 | 201.987 | 64.545 | 687.197 | 295.271 |
| 70 | 1093.91 | 403.776 | 118.715 | 1161 | 509.386 |

| time | 1 mM UTP, 1 mM AMP | 0.1 mM dITP, 0.1 mM AMP | 0.1 mM dITP, 0.3 mM AMP | 0.1 mM dITP, 1 mM AMP |
|---|---|---|---|---|
| 0 | 12.752 | 31.036 | 10.037 | 6.541 |
| 20 | 48.273 | 115.421 | 44.031 | 18.084 |
| 40 | 88.241 | 215.086 | 83.165 | 30.524 |
| 70 | 159.307 | 368.852 | 147.977 | 50.966 | grown overnight (about 18 hours) at 37° C. The $10^{-3}$ dilution yielded 195 colonies (i.e. 195 original cells), the $10^{-4}$ dilution yielded 23 colonies, and the $10^{-5}$ dilution yielded 2 colonies. To assay, 10 μL of each cell dilution were combined with 100 μL of each 1×L/L assay reagent and the light output measured with a Turner® TD-20/E luminometer at 0, 20, 50, and 80 minutes after addition of the L/L reagent. The resulting relative light unit values (rlu) are listed below as the raw data.

| 10 mM luciferin | 30 μL |
|---|---|
| 1M Hepes pH 7.8 | 150 μL |
| 1% gelatin | 300 μL |
| 1M MgSO$_4$ | 30 μL |
| 100 mM dCTP | 30 μL |
| 10 mM AMP | 9 μl |

| time (min) | 1 mM dCTP, 0.03 mM AMP | 1 mM dCTP, 0.05 mM AMP | 1 mM dCTP, 0.1 mM AMP | 0.5 mMdCTP 0.5 mMUTP, 0.03 mM AMP | 0.5 mMdCTP 0.5 mMUTP, 0.05 mMAMP | 0.5 mMdCTP 0.5 mMUTP, 0.1 mMAMP | 1 mM UTP, 0.03 mMAMP | 1 mM UTP, 0.05 mM AMP | 1 mM UTP 0.1 mM AMP |
|---|---|---|---|---|---|---|---|---|---|
| $10^{-3}$ cells | | | | | | | | | |
| 0 | 9.79 | 10.378 | 6.619 | 23.807 | 17.366 | 10.412 | 35.782 | 25.953 | 18.212 |
| 20 | 37.73 | 33.173 | 23.242 | 94.375 | 65.888 | 30.732 | 111.796 | 90.360 | 48.196 |
| 50 | 109.274 | 86.140 | 66.600 | 258.483 | 187.785 | 74.070 | 272.216 | 221.707 | 110.974 |
| 80 | 200.458 | 150.70 | 112.551 | 432.718 | 314.486 | 114.806 | 423.266 | 330.170 | 159.018 |
| $10^{-4}$ cells | | | | | | | | | |
| 0 | 8.213 | 9.464 | 6.397 | 23.506 | 18.381 | 10.109 | 36.780 | 26.666 | 18.709 |
| 20 | 10.470 | 11.393 | 8.144 | 28.818 | 23.070 | 10.634 | 44.263 | 34.123 | 21.579 |
| 50 | 18.861 | 17.758 | 12.861 | 43.965 | 35.117 | 13.234 | 60.015 | 45.916 | 28.489 |
| 80 | 31.281 | 25.697 | 18.100 | 60.292 | 46.183 | 15.938 | 72.830 | 54.561 | 32.186 |
| $10^{-5}$ cells | | | | | | | | | |
| 0 | 8.382 | 15.175 | 6.124 | 22.623 | 18.615 | 9.580 | 35.912 | 26.582 | 19.922 |
| 20 | 7.931 | 15.284 | 6.380 | 22.206 | 18.753 | 13.074 | 35.635 | 27.691 | 19.159 |
| 50 | 8.369 | 16.808 | 7.197 | 22.753 | 20.373 | 12.940 | 38.314 | 28.785 | 20.751 |
| 80 | 8.643 | 16.560 | 6.753 | 21.270 | 19.167 | 10.806 | 37.107 | 28.209 | 19.793 |
| no cells | | | | | | | | | |
| 0 | 9.491 | 18.175 | 7.151 | 26.867 | 20.228 | 13.168 | 41.544 | 30.528 | 22.319 |
| 20 | 10.478 | 19.634 | 8.134 | 28.019 | 22.421 | 15.633 | 42.952 | 31.305 | 26.204 |
| 50 | 12.457 | 21.535 | 9.798 | 32.242 | 24.947 | 20.378 | 47.039 | 33.756 | 33.473 |
| 80 | 13.916 | 23.146 | 10.88 | 34.432 | 26.586 | 23.605 | 47.17 | 33.553 | 37.734 |

In these data, 23 ($10^{-4}$ dilution) cells can easily be detected. It is possible that there was some level of detection at the 2 cell level because the slope of the line for the $10^{-5}$ dilution is greater than the slope for the no-cell control. With a decrease in cells, there is a sampling problem. Although two cells were sought to be plated, statistically, it is difficult to get an exact number of cells in each sample when so few cells are expected to be present.

EXAMPLE 19

Comparison of Two Luciferase Enzymes

Fifty milliliters of LB broth were inoculated with 50 μL of JM109 bacterial cells and grown for 2.5 hours, with shaking, at 37° C. The cells were then pelleted by centrifugation, washed three times with TBS and resuspended in 1 mL TBS. A serial dilution of the cell suspension was prepared, resulting in dilutions of $10^{-1}$, $10^{-2}$, $10^{-3}$, $10^{-4}$, and $10^{-5}$. The $10^{-2}$, $10^{-3}$, and $10^{-4}$ solutions were diluted 1:1 with TBS to make $5\times10^{-3}$, $5\times10^{-4}$, and $5\times10^{-5}$ dilutions of the original cell suspension. Ten microliters of each dilution were plated on an LB agar plate to determine the number of cells present.

Four tubes of L/L assay reagent were prepared by combining the following:

-continued

| 20% Chlorhexidine | 7.5 μL |
|---|---|
| 10 μg/mL Polymixin B Sulfate | 300 μL |
| water to a final volume of 3 mL | |

The following types and amounts of luciferase (all from Promega Corp.) were each added to a tube containing 3 mL of L/L assay reagent as described above:

| | | | Final Luciferase Concentration |
|---|---|---|---|
| 1. | Luc90-1B5, 3 mg/mL | 1 μL | 1 μg/mL |
| 2. | Luc90-1B5, 3 mg/mL | 10 μL | 10 μg/mL |
| 3. | Luc133-1B2, 1.6 mg/mL | 1.9 μL | 1 μg/mL |
| 4. | Luc133-1B2, 1.6 mg/mL | 19 μL | 10 μg/mL |

Ten microliters of each cell dilution, as well as a no-cell control, were added to 100 μL of each of the four types of L/L assay reagent. Samples were done in quadruplicate. The light output was measured at zero, 10, 20, 30, 42, 63, 90, 103, 116, 137, and 163 minutes after the addition of the L/L reagent on a Wallac Microbeta Jet Plate reader (1450) luminometer. The resulting average relative light outputs are listed below.

| time | 90-1B5 1 µg/mL | 90-1B5 10 µg/mL | 133-1B2 1 µg/mL | 133-1B2 10 µg/mL |
|---|---|---|---|---|
| | | 466 cells | | |
| 0 | 1010.7 | 6967.15 | 144.45 | 1349.225 |
| 9 | 2165.875 | 9989.65 | 255.55 | 2258.85 |
| 20 | 3346.65 | 11652.85 | 388.25 | 2551 |
| 31 | 5242.325 | 13912.4 | 580.55 | 3013.725 |
| 42 | 8287.35 | 18275.08 | 896.15 | 3718.475 |
| 63 | 16475.73 | 34131.95 | 1856.325 | 6274.675 |
| 90 | 25329.48 | 53716.38 | 3185.65 | 12218.05 |
| 103 | 28746.08 | 60039.08 | 3786.5 | 15390.53 |
| 116 | 31125.45 | 61949.45 | 4304.825 | 18936.5 |
| 137 | 34250.15 | 62517.33 | 5230.9 | 25667.5 |
| 163 | 37523.35 | 58539.8 | 6672.5 | 34681.6 |
| | | ~60 cells | | |
| 0 | 133.9 | 1015.55 | 23.05 | 232.9 |
| 9 | 406.025 | 1773.425 | 43.225 | 246.5 |
| 20 | 658.95 | 2097.85 | 62.325 | −307.65 |
| 31 | 1094.475 | 2602.9 | 84.975 | −857.975 |
| 42 | 1844.85 | 3457.675 | 118.725 | −1507.15 |
| 63 | 3748.725 | 6598.175 | 234.575 | −2439.88 |
| 90 | 5843.225 | 11190.18 | 445.575 | −2079.28 |
| 103 | 6729.225 | 12563.35 | 567.575 | −1569.83 |
| 116 | 7344.175 | 13237.48 | 683.9 | −709.225 |
| 137 | 8211.9 | 13551.2 | 864.475 | 884.225 |
| 163 | 9125.8 | 12512.45 | 1160.375 | 2739.05 |
| | | ~19 cells | | |
| 0 | 33.2 | 269.4 | 10.125 | 125.85 |
| 9 | 266.55 | 679.575 | 18.975 | 41.975 |
| 20 | 384.7 | 734.85 | 26.4 | −556.425 |
| 31 | 578.3 | 947.1 | 35.5 | −1190.98 |
| 42 | 870.15 | 1321.9 | 54.625 | −1945.45 |
| 63 | 1677.75 | 2862.675 | 129.5 | −3078.23 |
| 90 | 2713.125 | 5390.775 | 257.625 | −3058.08 |
| 103 | 3197.075 | 6197.475 | 329.05 | −2694.28 |
| 116 | 3572.5 | 6645.15 | 388.775 | −2137.83 |
| 137 | 4074.425 | 6915.025 | 466.9 | −1273.03 |
| 163 | 4605.6 | 6462.075 | 594.625 | −326.225 |
| | | ~3 cells | | |
| 0 | −56.98 | −375.75 | −0.75 | 28.45 |
| 9 | 3.155 | −200.325 | 0.325 | 111.025 |
| 20 | 11.39 | −354.625 | −3.975 | −350.825 |
| 31 | 39.875 | −322.3 | −8.3 | −910.225 |
| 42 | 82.895 | −272.575 | −11.3 | −1622.38 |
| 63 | 212.245 | 17.7 | −4.725 | −2803.15 |
| 90 | 389.35 | 537 | 19.425 | −2915.83 |
| 103 | 479.175 | 714.35 | 31.6 | −2627 |
| 116 | 540 | 822.925 | 43.425 | −2252.23 |
| 137 | 627.635 | 893.25 | 55.475 | −1895.35 |
| 163 | 715.905 | 835.725 | 76.575 | −1583.33 |

| Sample | Average slope | Upper 95% | Lower 95% |
|---|---|---|---|
| ~466 cells Luc90-1B5 1 µg/mL | 0.181 | 0.17 | 0.19 |
| ~466 cells Luc90-1B5 10 µg/mL | 0.053 | 0.486 | 0.0574 |
| ~466 cells Luc133-1B2 1 µg/mL | 0.1639 | 0.1454 | 0.1824 |
| ~466 cells Luc133-1B2 10 µg/mL | 0.0534 | 0.0508 | 0.056 |
| ~60 cells Luc90-1B5 1 µg/mL | 0.0876 | 0.0825 | 0.0928 |
| ~60 cells Luc90-1B5 10 µg/mL | 0.026 | 0.0235 | 0.0283 |
| ~60 cells Luc133-1B2 1 µg/mL | 0.0706 | 0.0664 | 0.0748 |
| ~60 cells Luc133-1B2 10 µg/mL | 0.0335 | 0.0318 | 0.035 |
| ~19 cells Luc90-1B5 1 µg/mL | 0.0498 | 0.0435 | 0.056 |
| ~19 cells Luc90-1B5 10 µg/mL | 0.014 | 0.0128 | 0.0162 |
| ~19 cells Luc133-1B2 1 µg/mL | 0.0476 | 0.0455 | 0.0498 |
| ~19 cells Luc133-1B2 10 µg/mL | 0.0297 | 0.0286 | 0.0309 |
| ~3 cells Luc90-1B5 1 µg/mL | 0.0099 | 0.00853 | 0.0113 |
| ~3 cells Luc133-1B2 1 µg/mL | 0.0164 | 0.0159 | 0.0169 |
| ~0.6 cells Luc90-1B5 1 µg/mL | 0.008 | 0.00473 | 0.0118 |
| ~0.6 cells Luc133-1B2 1 µg/mL | 0.0134 | 0.0128 | 0.014 |
| No cells Luc90-1B5 1 µg/mL | −0.00063 | −0.00128 | 0.0000286 |
| No cells Luc133-1B2 1 µg/mL | 0.0105 | 0.0094 | 0.0117 |

These results suggest that both luciferase enzymes are equally efficient at measuring regenerated ATP. Luciferase Luc90-1B5 appears to be slightly more efficient at 1 µg/mL and luciferase Luc90-1B5 is slightly more efficient at measuring ATP than is luciferase Luc133-1B2 at the higher enzyme concentration. Addition of the larger amount of enzyme causes the slope to fall by about five-fold. After about 1.5 hours, the reaction levels off.

As expected, the leveling off occurs faster when more enzyme is used. There is a similar trend between the data for 466 cells and 60 cells. One can detect 19 cells with both enzymes at both enzyme concentrations. These results also suggest that one can detect 3 cells with both enzymes. The fact that the "no cell" control for the luciferase Luc133-1B2 enzyme increases over time suggests the possibility of adenylate kinase activity in the Luc133-1B2 preparation. When data is analyzed differently, i.e. with the background subtracted, the two enzymes are not equally efficient due to the background present in Luc133-1B2 reactions that is not present in Luc90-1B5 reactions.

EXAMPLE 20

Heat Treatment to Reduce Background

A possible source of background luciferase values in no-cell control samples may be the presence of adenylate kinase in the preparation that is isolated from *E. coli*. This bacterial kinase enzyme may co-purify with the luciferase and function in the reaction to transfer phosphate from the dCTP to the AMP. In this example, the luciferase is heat-treated prior to use in order to destroy any adenylate kinase that might be present. The following conditions were used to heat treat Luc133-1B2 luciferase enzyme; 6.2 mg/mL enzyme was diluted 1:10 into each of the buffers.

1. 65° C., 20 minutes in 25 mM Hepes buffer, pH 7.8
2. 65° C., 20 minutes in 25 mM Hepes buffer, pH 7.8+0.1% gelatin
3. 65° C., 20 minutes in 25 mM Citrate buffer, pH 6.0
4. 65° C., 20 minutes in 25 mM Citrate buffer, pH 6.0+0.1% gelatin
5. 50° C., 20 minutes in 25 mM Citrate buffer, pH 4.5
6. no heat, enzyme in 25 mM Hepes buffer, pH 7.8+0.1 gelatin The following assay reagent was prepared:

| | |
|---|---|
| 10 mM luciferin | 120 μL |
| 1M Hepes, pH 7.8 | 600 μL |
| 1M MgSO$_4$ | 120 μL |
| 1% gelatin | 1200 μL |
| 100 mM dCTP | 120 μL |
| 10 mM AMP | 36 μL |
| 20% Chorhexidine | 30 μL |
| 10 mg/mL Polymixin B Sulfate | 1200 μL |
| sterile, nanopure water | 8572 μL |

The luciferase enzyme (six different treatments) was thereafter added to 1 mL of the above assay reagent to produce a set with a final concentration of 10 μg/mL and a set with a final luciferase concentration of 33 μg/mL. The background light output values were measured at 0, 28, and 69 minutes on a Wallac™ Plus plate reader luminometer (Microbeta Jet). This luminometer produces values about 1000-fold higher than the values that would be read on a Turner® TD-20/E luminometer. The resulting average relative light values are listed below. The first four treatments decreased background, while losing only about 15 to 20% activity.

| Sample | Activity | Normalized activity |
|---|---|---|
| pH 7.8 no gelatin (65° C.) | 995117.97 | 80.5% |
| pH 7.8 + gelatin (65° C.) | 1082095.37 | 87.5% |
| pH 6.0 no gelatin (65° C.) | 1032605.5 | 83.5% |
| pH 6.0 + gelatin (65° C.) | 1052804.97 | 85.2% |
| pH 4.5 (50° C.) | 78739.27 | 6.4% |
| pH 7.8 + gelatin, no heat | 1236286.53 | 100.0% | luciferases used were Luc133-1B2 and Luc146-1H2. Both enzymes were heat-treated for 60 minutes at 65° C. to inactivate any adenylate kinase that might be present in the luciferase preparation.

The following assay reagent was prepared and divided in half. Each half was then combined with either Luc133-1B2 or Luc146-1H2 heat-treated luciferase to a final enzyme concentration of 33 μg/mL.

| Assay Reagent | Volume |
|---|---|
| 10 mM luciferin | 120 μL |
| 1M Hepes, pH 7.8 | 600 μL |
| 1M MgSO$_4$ | 120 μL |
| 1% gelatin | 1200 μL |
| 100 mM dCTP | 120 μL |
| 10 mM AMP | 120 μL |
| 20% chlorhexidine | 30 μL |
| 10 mg/mL Polymixin B Sulfate | 1200 μL |
| water | 7851 μL |

JM109 *E. coli* cells were grown for 3 hours at 37° in LB broth. They were washed three times with 1×TBS and 1:10 serial dilutions were prepared in TBS. Ten microliters of each dilution were added to a well of a 96 well plate and 100 μL of the Luciferase/Luciferin assay reagent. The light output was measured on a Wallace Microbeta jet (1450) plate reader luminometer at 0, 24, and 94 minutes. The relative light unit values are below. The $10^{-6}$ dilution had about 3 cells the $10^{-5}$ had about 32 cells and the $10^{-4}$ had about 203 cells.

| | Luciferase Luc133-1B2 | | | | Luciferase Luc146-1H2 | | | |
|---|---|---|---|---|---|---|---|---|
| | $10^{-3}$ | $10^{-4}$ | $10^{-5}$ | $10^{-6}$ | $10^{-3}$ | $10^{-4}$ | $10^{-5}$ | $10^{-6}$ |
| t = 0 | | | | | t = 0 | | | |
| ave | 1115 | 1514 | 1135 | 1130 | ave 357 | 504 | 411 | 351 |
| sd | 33.6 | 93.6 | 23.8 | 22.8 | sd 44.2 | 130 | 114 | 6.7 |
| % cv | 0.0301 | 0.0618 | 0.021 | 0.02 | % cv 0.12 | 0.25 | 0.27 | 0.02 |
| t = 25 min | | | | | t = 25 min | | | |
| ave | 785 | 2395 | 956 | 834 | ave 315 | 1078 | 437 | 323 |
| sd | 30.8 | 227 | 40.5 | 33.5 | sd 32.4 | 120 | 100 | 10.4 |
| % cv | 0.04 | 0.1 | 0.04 | 0.04 | %cv 0.1 | 0.1 | 0.2 | 0.03 |
| t = 94 min | | | | | t = 94 min | | | |
| ave | 1952 | 5360 | 2364 | 2117 | ave 328 | 3444 | 753 | 365 |
| sd | 85.44 | 771 | 123 | 105 | sd 29.8 | 325 | 124 | 19.8 |
| % cv | 0.04 | 0.14 | 0.05 | 0.05 | % cv 0.09 | 0.09 | 0.16 | 0.05 |

EXAMPLE 21

Use of Luciferase Luc146-1H2 in an ATP Generation Assay

In this study, the activity of two thermostable luciferases was compared in an ATP generation assay. The two To determine if the background (TBS) values were different from the $10^{-6}$ diluted samples, a Student's T-test was performed. When all of the data points are used for t=0, the sample means are the same. This means that they start at the same mean. At the t=94 minute data points, the means are different if all of the time points are used. For Luc133-1B2, if TBS and $10^{-6}$ samples are compared, these are close spatially on the plate and the means are not different at t=94 min, so it is not possible to detect 3 cells with this enzyme. The difference that is seen when all of the data points are used is likely due to a bias. The $10^{-6}$ samples have a slightly longer time to incubate because of the way the plate is set up. The means of the TBS and $10^{-6}$ sample, when tested with the luciferase Luc146-1H2 are clearly different (samples close together on the plate were compared). The luciferase Luc133-1B2 enzyme has more background than the luciferase Luc146-1H2 enzyme. The Luc133-1B2 enzyme preparation may be less pure than that of the Luc146-1H2 enzyme.

It was also determined from these data that the Luc146-1H2 enzyme has a more linear response for its slope on a rlu vs time graph.

EXAMPLE 22

Detection of Four Cells of an Exponentially Grown E. coli Culture

In this Example, the Luc146-1H2 thermostable luciferase was assayed with both an overnight (about 30 hours) and an exponential E. coli culture to further illustrate the efficiency of a process of the invention.

For the exponential culture, JM109 cells E. coli (50 μL) were grown in 50 mL of LB broth for 3.5 hours. A similar culture was prepared the day before and permitted to grow for 20 hours. Both cultures were grown, with shaking, at 37° C.

The cells were diluted in TBS in an attempt to make their optical densities equal. One hundred microliters of the overnight culture were combined with 900 μL of TBS, whereas 188 μL of the exponentially growing culture were combined with 812 μL of TBS. The assay reagent was prepared as described in Example 21 with the heat-treated Luc146-1H2 luciferase enzyme added to a final concentration of 33 μg/mL.

Six milliliters of the luciferase/luciferin assay reagent were then added to each of four tubes. dCTP was added to the tubes to the final concentrations of 0.3 mM, 0.5 mM, 1 mM, and 2 mM. Ten microliters of each cell dilution were added to 100 μL of the L/L reagent in a 96-well plate and the light output was measured with a Wallac™ Microbeta Jet 1450 plate reader luminometer. The average relative light unit (rlu) values obtained from 6 replicates at 0, 32, and 88 minutes are listed below.

The two bacterial cultures were serially diluted and 10 μL plated onto a LB agar plate to determine the number of colonies. There was about a 10 fold difference between the overnight and the 3.5 hour culture. The difference in the cell numbers could be caused by difference in the cell morphology resulting in faulty OD readings. The $10^{-6}$ dilution of overnight culture resulted in 31 colonies, the $10^{-5}$ dilution resulted in 210 colonies. For the exponential culture, the $10^{-6}$ dilution of resulted in 4 colonies, the $10^{-5}$ dilution resulted in 47 colonies, and the $10^{-4}$ dilution resulted in 348 colonies.

Overnight culture, 31 cells rlu values

| Time | 0.3 mM | 0.5 mM | 1 mM |
|---|---|---|---|
| 0 | 7.4 | 5.9 | 2.5 |
| 32 | 14.9 | 13.3 | 13.7 |
| 88 | 25.6 | 8.6 | 29.6 |

Overnight culture, 210 cells rlu values

| Time | 0.3 mM | 0.5 mM | 1 mM |
|---|---|---|---|
| 0 | 17.2 | 18.1 | 21.4 |
| 32 | 71.5 | 78.4 | 96.5 |
| 88 | 189.1 | 188.6 | 252.2 |

Overnight culture, about 2100 cells rlu values

| Time | 0.3 mM | 0.5 mM | 1 mM |
|---|---|---|---|
| 0 | 87.9 | 126.1 | 177.7 |
| 32 | 607.3 | 702.1 | 904 |
| 88 | 1726.2 | 1879.4 | 2385.2 |

Exponential culture, 4 cells rlu values

| Time | 0.3 mM | 0.5 mM | 1 mM |
|---|---|---|---|
| 0 | 2.3 | 4.5 | 2.6 |
| 32 | 6.7 | 4.8 | 9.1 |
| 88 | 18.9 | 12.8 | 23.1 |

Exponential culture, 49 cells rlu values

| Time | 0.3 mM | 0.5 mM | 1 mM |
|---|---|---|---|
| 0 | 4.9 | 3.7 | 5.8 |
| 32 | 29.8 | 29.5 | 42.1 |
| 88 | 128.8 | 85.1 | 115.9 |

Exponential culture 348 cells rlu values

| Time | 0.3 mM | 0.5 mM | 1 mM |
|---|---|---|---|
| 0 | 18 | 3.7 | 5.8 |
| 32 | 29.8 | 278.6 | 395.96 |
| 88 | 1359.7 | 813.4 | 1123.2 |

Statistical analysis for the 4 cell data set:
for t=0
timepoint
t-Test: Two-Sample Assuming
Equal Variances

|  | Variable 1 | Variable 2 |  |
| --- | --- | --- | --- |
| Mean | 148.1333 | 150.6833 | for 1 mM dCTP the means |
| Variance | 11.7907 | 4.6457 | of the TBS and $10^{-6}$ |
| Observations | 6 | 6 | sample |
| Pooled Variance | 8.2182 |  | are the same at the t = 0 timepoint |
| Hypothesized Mean Difference | 0 |  |  |
| df | 10 |  |  |
| t Stat | −1.5407 |  |  |
| P(T <= t) one-tail | 0.07721 |  |  |
| t Critical one-tail | 1.8125 |  |  |
| P(T <= t) two-tail | 0.1544 |  |  |
| t Critical two-tail | 2.2281 |  |  |
| Mean | 135.3833 | 158.4667 | For 1 mM the means |
| Variance | 10.1977 | 145.7267 | of the TBS and $10^{-6}$ |
| Observations | 6 | 6 | timepoint are different at the |
| Pooled Variance | 77.9622 |  | t = 88 minute timepoint |
| Hypothesized Mean Difference | 0 |  |  |
| df | 10 |  |  |
| t Stat | −4.5281 |  |  |
| P(T <= t) one-tail | 0.000547 |  |  |
| t Critical one-tail | 1.8125 |  |  |
| P(T <= t) two-tail | 0.001095 |  |  |
| t Critical two-tail | 2.2281 |  |  | for t = 88 min timepoint
t-Test: Two-Sample Assuming Equal Variances

The 1 mM concentration of dCTP provides the greatest level of detection. The slopes are steeper on rlu vs time graphs, and one can detect a small number of cells with this concentration of dCTP. The 31 cell sample for the overnight culture showed a similar response to that of the 4 cell sample of the exponential culture. Possible reasons for this observation are that the stationary cells have tougher cell walls and the lysis reagents may not be sufficient to completely lyse these cells. Because the stationary cells have been growing longer it is also possible that there are byproducts produced that are inhibiting the regeneration of ATP. In addition, stationary cells might not be producing the phosphate transfer enzymes as readily as the exponentially growing cells. However, it is clear that the 4 cell detection of the exponentially growing culture and the 31 cell detection of the overnight culture are statistically significant.

EXAMPLE 23

Bacterial Detection in Apple Juice and Cherry Juice with Thermostable Luciferase Luc146-1H2

This example demonstrates the ability of the thermostable luciferase, Luc146-1H2, to detect bacteria in both apple juice and cherry juice to a sensitivity of about 44 cells in apple juice and 63 cells in cherry juice. These were the lowest dilutions tested in this experiment.

One milliliter of an overnight JM109 culture in LB broth was centrifuged in a microcentrifuge. The supernatant was removed and the cellular pellet resuspended in 1 mL of 1×TBS. This bacterial solution was serially diluted 1:10 in TBS to produce 1:100,00 and 1:1,000,000 dilutions. Fifty microliters of each of these two dilutions was plated on LB agar plates and incubated overnight at 37° C. The colonies were counted and it was determined that the 50 μL from the 1:100,000 dilution had 235 cells and the 50 μL from the 1:1,000,000 dilution had 44 cells for the cell dilutions used to test apple juice. The 50 μL from the 1:100,000 dilution had 448 cells and the 50 μL from the 1:1,000,000 dilution had 63 cells for the cell dilutions used to test cherry juice. Ten microliters of the each dilution was placed into separate 1 mL aliquots of apple juice and also into separate 1 mL aliquots of cherry juice. The solutions were mixed and each was passed through a separate Gelman 13 mm, 0.45 micron filter. The filters were washed twice with 500 μl 1×TBS. Then the center of each filter was removed with a hole puncher and placed in a separate luminometer tube. Five replicates of each sample were prepared. Control samples containing no cells were also prepared.

L/L assay reagent with nucleotides was prepared by combining the following:

| | |
| --- | --- |
| 100 μM Luciferin | 30 μL |
| 50 mM Hepes, pH 7.8 | 150 μL |
| 0.62 mg/mL luciferase Luc146-1H2 | 160 μL |
| 1M MgSO$_4$ | 30 μL |
| 1 percent gelatin | 300 μL |
| 100 mM dCTP | 30 μL |
| 100 mM AMP | 3 μL |
| 20% chlorhexidine (add last) | 300 μL |
| 10 mg/mL Polymixin B Sulfate | 300 μL |
| water | 1990 μL |

One hundred microliters of the L/L assay reagent was combined with each filter in a luminometer tube. The light output was measured immediately and then every 15 minutes for the next hour on a Turner TD-20/E luminometer. The resulting average relative light values are listed below.

| | Cherry Juice | | |
| --- | --- | --- | --- |
| Time | control (0 cells) | 448 cells | 63 cells |
| 0 | 5.78 | 5.78 | 5.56 |
| 15 | 5.41 | 6.56 | 6.04 |
| 30 | 5.49 | 7.24 | 6.4 |
| 45 | 5.35 | 8.08 | 6.51 |
| 60 | 6.33 | 9.99 | 8.04 |

| | Apple Juice | | |
| --- | --- | --- | --- |
| Time | control (0 cells) | 235 cells | 44 cells |
| 0 | 6.89 | 7.14 | 6.72 |
| 15 | 6.25 | 8.49 | 7.39 |
| 20 | 6.09 | 9.07 | 7.53 |
| 45 | 6.48 | 10.62 | 8.49 |
| 60 | 7.45 | 12.7 | 9.78 |

EXAMPLE 24

Detection of ATP Using Fluorescence-based Methods

In addition to detecting ATP by luciferase-based methods, ATP can be detected using fluorescence-based systems. For the fluorescence-based measurements, an ATP determination kit was used (Sigma #366-A Lot#117H6017). This kit uses a combination of phosphoglycerate kinase and glyceraldehyde phosphate dehydrogenase, to catalyze the formation of NAD from NADH in the presence of ATP. Since the NADH is fluorescent, but the NAD is not, ATP can be measured as a loss in fluorescence intensity.

The reaction buffer was prepared from kit components as follows: 3 mL supplied buffer solution was diluted in 5.25 mL nanopure water, and 0.75 mL 12 percent trichloroacetic acid was added. One vial of the supplied NADH was reconstituted in 1 mL nanopure water; the enzyme mix was used as supplied. For each measurement, 10 μL enzyme mix and 20 μL NADH were added to 1.5 mL of reaction buffer in a clear plastic 10 mm cuvette. Fluorescence was read in a SPEX Fluorolog Fluorimeter using SPEX dm3000 Software, with absorbance and emission wavelengths set at 340 nm and 460 nm, respectively.

| ATP Conc. | Volume Added | Mass Added | Decrease In Fluorescence Units In 10,000's | | |
|---|---|---|---|---|---|
| 10 mM | 20 μl | 200 nmoles | 135 | nd[a] | nd[a] |
| 1 mM | 20 μl | 20 nmoles | 84.3 | 132 | nd[a] |
| 1 mM | 10 μl | 10 nmoles | 89.3 | nd[a] | nd[a] |
| 1 mM | 5 μl | 5 nmoles | 76.4 | nd[a] | nd[a] |
| 100 μM | 40 μl | 4 nmoles | 66.7 | 60.2 | nd[a] |
| 100 μM | 20 μl | 2 nmoles | 23.9 | 21.9 | 20.8 |
| 100 μM | 10 μl | 1 nmole | 19.1 | 22.0 | 18.9 |
| 100 μM | 5 μl | 500 pmoles | 7.6 | 6.9 | 6.8 |
| 10 μM | 20 μl | 200 pmoles | 11.6 | 10.0 | 11.1 |
| 10 μM | 10 μl | 100 pmoles | 10.4 | 6.9 | 6.6 |
| 1 μM | 20 μl | 20 pmoles | 8.2 | 8.4 | 5.2 |
| 1 μM | 10 μl | 10 pmoles | 8.0 | 8.1 | 5.3 |
| 0.1 μM | 20 μl | 2 pmoles | 3.2 | 5.6 | 3.6 |
| 0.01 μM | 20 μl | 200 fmoles | 8.1 | 9.7 | 6.8 |
| Tris | 20 μl | — | 4.3 | 3.7 | 3.8 |
| Tris | 10 μl | — | 4.0 | 3.3 | 3.5 |

[a]nd, not done.

ATP samples at various concentrations were prepared by serially diluting ATP tenfold into 10 mM Tris, pH 7.3. Varying amounts of each dilution was added to the cuvette and the observed decrease in fluorescence is shown in the table below. For comparison ATP was also quantified using luciferase. 20 μL of each ATP dilution was added to 100 μL LAR with 10 ng luciferase and light output was measured using a TD-20e luminometer. Each dilution was measured in duplicate and the data are in the table below.

| ATP, 20 μL of | Light Units | |
|---|---|---|
| 10 mM | 102,417 | 102,731 |
| 1 mM | 117,718 | 98,842 |
| 100 μM | 47,676 | 44,101 |
| 10 μM | 7690 | 6998 |
| 1 μM | 812 | 798 |
| 0.1 μM | 76.8 | 67.8 |
| 0.01 μM | 7.0 | 4.5 |
| Tris | 0.06 | 0.06 |

This example indicates that ATP can be detected by at least two separate methods. In the fluorescence-based system, changes of approximately 200,000 fluorescent light units were significant, which corresponds to 1 nanomole ATP. The luciferase assay was sensitive to lower levels of ATP.

EXAMPLE 35

Detection of ATP Using Fluorescence: Cell Lysates

ATP can also be generated by incubating cell lysates with AMP and dCTP. The Sigma ATP determination kit described in Example 24 was also used to detect ATP in this system. Reactions were assembled as described in the table below and incubated at room temperature. ATP concentrations were quantified at 80 minutes and 140 minutes using luciferase.

| Reaction | E. coli Lysate | 0.05M MgSO$_4$ | 10 mM AMP | 100 mM dCTP |
|---|---|---|---|---|
| 1 | 100 μL | 20 μL | 20 μL | 10.5 μL |
| 2 | — | 20 μL | 20 μL | 10.5 μL |
| 3 | 100 μL | — | 20 μL | 10.5 μL |
| 4 | 100 μL | 20 μL | — | 10.5 μL |
| 5 | 100 μL | — | — | 10.5 μL |

In this assay 15 μL each reaction was added to 100 μL LAR and 10 ng luciferase. Light output was measured using a Turner Luminometer TD-20e (Table 63). During the time course, ATP was also measured by fluorescence. The procedure was as described in Example 33, except that 15 μL each reaction was added per reading, instead of 20 μL. The first set of time points began at 80 minutes; the second set of readings began at 140 minutes. Each reaction was assayed in duplicate or triplicate, and the results are shown in the table below.

This example demonstrates that ATP synthesized in cell lysates can be detected using a luciferase or a fluorescence assay.

| | Light Units | |
|---|---|---|
| Reactions | T = 80 Minutes | T = 140 Minutes |
| 1 | 33,519 | 65,522 |
| 2 | 2.158 | 2.086 |
| 3 | 362.7 | 370.6 |
| 4 | 0.5 | 0.561 |
| 5 | 1.898 | 1.057 |

From the foregoing, it will be observed that numerous modifications and variations can be effected without departing from the true spirit and scope of the present invention. It is to be understood that no limitation with respect to the specific examples presented is intended or should be inferred. The disclosure is intended to cover by the appended claims modifications as fall within the scope of the claims.

What is claimed is:

1. A method for determining the presence of cells in an aqueous sample composition that comprises the steps of:

(a) admixing said aqueous sample composition with a high energy phosphate donor other than ADP to form a reaction mixture, said cells, when present, being treated to form ATP in said reaction mixture;

(b) maintaining said reaction mixture for a time period sufficient for enzymes endogenous to the cells to convert adenosine present to ATP; and (c) assaying for the presence of ATP, the presence of ATP indicating the presence of cells in said aqueous sample.

2. The method according to claim 1 wherein AMP is further admixed in the reaction mixture of step (a).

3. The method according to claim 1 wherein ATP is assayed using a luciferase enzyme.

4. The method according to claim 3 wherein said luciferase enzyme is added to the admixture of step (a).

5. The method according to claim 3 wherein said luciferase enzyme is a thermostable luciferase.

6. The method according to claim 5 wherein said thermostable luciferase enzyme is heat-treated.

7. The method according to claim 6 wherein said thermostable luciferase enzyme is Luc146-1H2.

8. The method according to claim 1 wherein the high energy phosphate donor other than ADP is a nucleotide or deoxynucleotide triphosphate other than ADP.

9. The method according to claim 8 wherein the high energy phosphate donor is dCTP.

10. The method according to claim 1 wherein the cells in a test sample are treated to form an aqueous sample composition.

11. The method according to claim 10 wherein a sample source is filtered to form a test sample on a filter.

12. The method according to claim 10 wherein the cells are treated by admixing a test sample with an extractant.

13. The method according to claim 12 wherein the extractant and high energy phosphate donor are admixed together with said test sample.

14. The method according to claim 12 wherein the test sample is a surface to be analyzed.

15. The method according to claim 12 wherein said extractant comprises polymixin B sulfate.

16. The method according to claim 15 wherein said extractant further comprises chlorhexidine.

17. The method according to claim 16 wherein said polymixin B sulfate is present at a concentration of about 0.5 percent to about 5 percent and said chlorhexidine is present at a concentration of about 0.1 percent to about 2 percent.

18. The method according to claim 1 wherein magnesium ion is also admixed in step (a).

19. The method according to claim 1 wherein the aqueous sample composition is derived from a liquid sample source.

20. The method according to claim 1 wherein the aqueous sample composition is derived from a sample source that is a food or beverage.

* * * * *